United States Patent
Seko et al.

(10) Patent No.: US 8,600,129 B2
(45) Date of Patent: Dec. 3, 2013

(54) ULTRASONIC VOLUME DATA PROCESSING DEVICE

(75) Inventors: Koji Seko, Oume (JP); Yuko Nagase, Mitaka (JP); Hirohiko Narita, Oume (JP); Atsuko Yokoi, Oume (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 277 days.

(21) Appl. No.: 12/902,269

(22) Filed: Oct. 12, 2010

(65) Prior Publication Data

US 2011/0091086 A1 Apr. 21, 2011

(30) Foreign Application Priority Data

Oct. 15, 2009 (JP) ................................. 2009-238767
Oct. 15, 2009 (JP) ................................. 2009-238768

(51) Int. Cl.
*G06K 9/00* (2006.01)
*G06K 9/34* (2006.01)

(52) U.S. Cl.
USPC .............................. 382/128; 382/154; 382/173

(58) Field of Classification Search
USPC .......................................... 382/128, 154, 173
See application file for complete search history.

(56) References Cited

U.S. PATENT DOCUMENTS

| 5,734,384 | A | 3/1998 | Yanof et al. | |
|---|---|---|---|---|
| 6,429,884 | B1 | 8/2002 | Budz et al. | |
| 6,542,153 | B1 * | 4/2003 | Liu et al. | 345/424 |
| 6,724,938 | B1 * | 4/2004 | Matsumura | 382/199 |
| 7,433,504 | B2 * | 10/2008 | Deischinger et al. | 382/128 |
| 8,077,948 | B2 * | 12/2011 | Gindele et al. | 382/128 |
| 8,103,066 | B2 * | 1/2012 | Kim et al. | 382/128 |
| 8,149,236 | B2 * | 4/2012 | Nakao et al. | 345/423 |
| 2004/0253572 | A1 * | 12/2004 | Chosack et al. | 434/268 |
| 2006/0058605 | A1 * | 3/2006 | Deischinger et al. | 600/407 |
| 2010/0030079 | A1 | 2/2010 | Hamada | |

FOREIGN PATENT DOCUMENTS

| JP | 06-028489 A | 2/1994 |
|---|---|---|
| JP | 11-221220 A | 8/1999 |
| JP | 3015728 B2 | 3/2000 |

(Continued)

OTHER PUBLICATIONS

European Search Report dated Mar. 4, 2011, issued in corresponding European Patent Application No. 10013335.4.

(Continued)

*Primary Examiner* — Utpal Shah
(74) *Attorney, Agent, or Firm* — Westerman, Hattori, Daniels & Adrian, LLP

(57) ABSTRACT

An ultrasonic volume data processing device which forms a three-dimensional image of a target tissue in a living body is provided. A range in which a rendering process is applied is limited by a three-dimensional region of interest (3D-ROI). The three-dimensional region of interest has a clipping plane as a rendering start surface. A shape of the clipping plane can be deformed into a convex shape or a concave shape by a user operation, and the clipping plane may be freely inclined in two-dimensional directions. With this configuration, for example, the clipping plane can be suitably positioned in a gap between a face of a fetus and a placenta. When the curved clipping plane is used, a striped pattern noise tends to be formed in the three-dimensional image. In order to resolve or reduce the striped pattern noise, a special voxel calculation is applied to a final voxel of each ray in the voxel calculation for each ray.

23 Claims, 15 Drawing Sheets

(56) References Cited

FOREIGN PATENT DOCUMENTS

| JP | 2000-339486 | A | 12/2000 |
|---|---|---|---|
| JP | 2001-145631 | A | 5/2001 |
| JP | 3410404 | B2 | 5/2003 |
| JP | 2004-033658 | A | 2/2004 |
| JP | 2004-113603 | A | 4/2004 |
| JP | 2006-055506 | A | 3/2006 |
| JP | 2006-061698 | A | 3/2006 |
| JP | 2006-087601 | A | 4/2006 |
| JP | 2006-167100 | A | 6/2006 |
| JP | 2006-218210 | A | 8/2006 |
| JP | 2006-223712 | A | 8/2006 |
| JP | 2008-113868 | A | 5/2008 |
| JP | 2008-178662 | A | 8/2008 |

OTHER PUBLICATIONS

Robert, Bruno et al.; "An Interactive Tool to Visualize Three-Dimensional Ultrasound Data"; Ultrasound in Med. & Biol., vol. 26, No. 1, 2000, pp. 133-142.

Weiler, Manfred et al.; "Direct volume rendering in OpenSG"; Elsevier; Computers & Graphics, vol. 28, 2004, pp. 93-98.

European Search Report dated Jun. 8, 2011, issued in corresponding European Patent Application No. 10013335.4.

Karadayi, Kerem et al.; "Three-Dimensional Ultrasound: From Acquisition to Visualization and From Algorithms to Systems"; IEEE Reviews in Biomedical Engineering, USA, vol. 2, Jan. 1, 2009, pp. 23-29, XP011284052.

Roettger, Stefan et al.; "Smart Hardware-Accelerated Volume Rendering"; Proceedings of the Joint Eurographics and IEEE TCVG Symposium on visualization, Data Visualization, Jan. 1, 2003, pp. 231-301, XP008059777.

European Search Report dated Mar. 22, 2012, issued in corresponding application No. 12000104.5.

Tatarchuk, et al., "Advanced interactive medical visualization on the GPU", Journal of Parallel and Distributed Computing, vol. 68, No. 10. dated Oct. 1, 2008, pp. 1319-1328, XP025428727. European Search Report dated Mar. 22, 2012.

Zhang, et al., "High-quality cardiac image dynamic visualization with feature enhancement and virtual surgical tool inclusion", The Visual Computer; International Journal of Computer Graphics, dated Apr. 24, 2009, vol. 25, No. 11, pp. 1019-1035, XP019759196. European Search Report dated Mar. 22, 2012.

Zhang, et al., "GPU-Based Image Manipulation and Enhancement Techniques for Dynamic Volumetric Medical Image Visualization", Biomedical Engineering From Nano to Macro. IEEE International Symposium, dated Apr. 1, 2007, pp. 1168-1171, XP031064487.

Karadayi, et al., "Artifact-free volume clipping algororithm for real-time 3d ultrasound", SPIE 6513, 651311—Medical Imagine 2007; Ultrasonic Imaging and Signal Processing, dated Feb. 28, 2007, vol. 6513, pp. 1-11, XP040237549, European Search Report dated Mar. 22, 2012.

Manssour, et al., "Visualizing inner structures in multimodal volume data", Computer Graphics and Image Processing, 2002 Proceedings XV Brazilia Symposium, dated Oct. 7, 2002, pp. 51-58, XP010624491. European Search Report dated Mar. 22, 2012.

European Search Report dated Apr. 16, 2012, issued in corresponding application No. 10 013 335.4.

Sun et al., "Feature-Based Interactive Visualization of Volumetric Medical Data", Systems, Man, and Cybernetics, 1998. 1998 IEEE International Conference E on San Diego, CA, USA Oct. 10-14, 1998, vol. 2, pp. 1162-1167, XP010311072. European Search Report dated Apr. 16, 2012.

Japanese Notice of Grounds for Rejection dated Sep. 17, 2013, issued in Japanese Patent Application No. 2009-238767, w/partial English translation and additional explanation of notice.

Japanese Notice of Grounds for Rejection dated Sep. 17, 2013, issued in Japanese Patent Application No. 2009-238768.

* cited by examiner

ULTRASONIC VOLUME DATA PROCESSING DEVICE

BACKGROUND

1. Technical Field

The present invention relates to an ultrasonic volume data processing device, and in particular, to a setting technique of a three-dimensional region of interest (3D-ROI) for limiting a range within which a three-dimensional image process is applied.

2. Background Art

In recent years, in the medical field, three-dimensional ultrasonic diagnosis is becoming widespread. For example, in the field of obstetrics, ultrasound is transmitted to and from a three-dimensional space including a fetus in the mother (transmission and reception space), and volume data (three-dimensional ultrasonic data) are obtained. A rendering process is applied to the volume data to form a three-dimensional image of the fetus. As a method of forming the three-dimensional image, methods such as volume rendering are known. In volume rendering, a plurality of rays (lines of sight) are set passing through the space for which the image is to be formed, and a voxel calculation is successively executed from a start point to an end point on each ray. A final result of the voxel calculation for each ray is set as a pixel value of the ray. A three-dimensional image is formed as a collection of a plurality of pixel values calculated for the plurality of rays. Other known image processing methods include surface rendering, accumulated projection, etc.

When a three-dimensional image of a target tissue to be formed into an image is to be formed, it is desirable to prevent, to the extent possible, image formation of other tissues (non-target tissues) adjacent to the target tissue. More specifically, in the volume rendering, during the process of proceeding with the voxel calculation on each ray, if the voxel calculation is also applied to other tissues existing at a nearer side (side near the viewpoint) of the target tissue, a problem may occur in that the target tissue is hidden behind the other tissues and the target tissue cannot be observed in the three-dimensional image which is ultimately formed. For example, in a three-dimensional image representing the fetus in the womb, there may be a problem in that the face of the fetus, which is most desired to be observed, is hidden behind the placenta existing in front of the fetus.

In consideration of this, a three-dimensional region of interest (3D-ROI) is employed. The three-dimensional region of interest generally is a partial space existing in a three-dimensional data processing space, and is a space for limiting the range within which the rendering process is applied. The above-described problem can be solved by setting the three-dimensional region of interest in the three-dimensional data processing space in a manner such that the fetus (more specifically, data corresponding to the fetus) is positioned in the three-dimensional region of interest and the placenta (more specifically, data corresponding to the placenta) is positioned outside of the three-dimensional region of interest. In the three-dimensional data processing space, the three-dimensional region of interest is conceptually viewed as a three-dimensional figure. Normally, the three-dimensional region of interest has a rendering start surface. For example, when a three-dimensional image of a fetus is formed, the rendering start surface is manually or automatically set such that the rendering start surface is positioned between the face of the fetus and the placenta. Because the rendering start surface has a tissue-separating function, the rendering start surface may be called a clipping plane.

Background Art Reference 1 (JP 2004-113603 A) discloses a technique for changing a shape of the three-dimensional region of interest. According to this technique, a cubic shape with a particular corner portion cut out in a slanted manner may be created as the three-dimensional region of interest. Background Art Reference 2 (JP 2004-33658 A) discloses a three-dimensional region of interest having a free curved surface defined based on a plurality of points. Background Art Reference 3 (JP 2006-61698 A (U.S. Pat. No. 7,433,504)) discloses a three-dimensional region of interest having a free curved surface. In the technique disclosed in Background Art Reference 3, the shape of the free curved surface is defined by designation of the coordinates by the user on two orthogonal cross sections. A special point called a virtual point is used in order to reflect the coordinate designation for one cross section to the other cross section. Background Art Reference (JP 2001-145631 A) discloses a technique for automatically setting the three-dimensional region of interest. Background Art Reference 5 (JP 2000-339486 A) discloses a technique for changing a sampling interval in order to prevent formation of a striped pattern caused by the volume rendering.

Because the tissue for which an image is desired to be formed and the shape of the tissue for which an image is not desired to be formed have various shapes in the living body, it is not suitable to employ a simple cubic shape as the shape of the three-dimensional region of interest. In particular, when the clipping plane which is the rendering start surface is set as a simple plane, it would become difficult to sufficiently separate a tissue for which the image is to be formed and the tissue for which the image is not to be formed. Therefore, the technique described in Background Art Reference 1 cannot be employed.

Meanwhile, in order to reduce the load of the user and shorten the examination time, it is desired that the three-dimensional region of interest can be set easily and quickly. In particular, it is desired that the position, shape, and orientation of the rendering start surface can be set easily and quickly. However, because the technique described in Reference 2 requires that a plurality of points be individually positioned along the shape of the surface of the tissue on a tomographic image, a load for the operation tends to be imposed.

Research conducted by the present inventors has revealed that, in many cases, the surface shape of the tissue for which an image is to be formed and the surface shape of the tissue for which an image is not to be formed are either approximate convex surfaces or approximate concave shapes. In addition, it is found that, in many cases, the gap between the tissues is inclined with respect to a center axis of the three-dimensional region of interest (rendering center line). Based on this knowledge from experiences, the technique disclosed in Background Art Reference 3 cannot be employed in order to sufficiently separate the target tissue. Although the technique of Background Art Reference 3 can freely change the shape of the upper surface (clipping plane) of the three-dimensional region of interest, the overall inclination of the upper surface cannot be changed. The height of the four corners of the upper surface is always the same, and inserting the upper surface in an inclined gap is extremely difficult. In the technique disclosed in Background Art Reference 3, the three-dimensional region of interest itself may be inclined relative to the volume data. However, in this case, other problems may occur, such as a change in the rendering direction or inclination, in the three-dimensional region of interest, of a tissue for which an image formation is not required. The above-described problem is a first problem to be solved.

In the case where the volume rendering is executed using the three-dimensional region of interest, if one or both of a start surface and an end surface of rendering is curved, the path lengths of the rays would not be uniform. If an array of sampling points is determined with a predetermined sampling interval based on a particular regularity on the rays, there is a problem that a periodicity is generated along the curving direction, and a striped pattern is formed on the ultrasonic image. For example, when the clipping plane (that is, the rendering start surface) is a convex spherical surface or a concave spherical surface, a striped pattern of a multiple-ring shape tends to be formed, and, when the clipping plane has a shape such as a semi-cylinder, a vertical striped pattern tends to be formed. In particular, when a strong reflective object is present around the end surface, such a problem becomes significant. When the array of sample points is matched among the plurality of rays, the start surface would become a stair shape. In this case, if a strong reflective object exists near the start surface, a striped pattern tends to form to a significant extent. In either case, when the path lengths and positions are not uniform among the plurality of rays, the above-described problem tends to occur. As such a striped shape significantly degrades the appearance of the three-dimensional ultrasonic image and obscures disease diagnosis, inhibition of the striped pattern is strongly desired. This problem is a second problem to be solved.

SUMMARY (1) Solution to First Problem

A first advantage of the present invention is that an orientation of the clipping plane in the three-dimensional region of interest to which the rendering is applied can be suitably set. In other words, the first advantage is that an orientation and a shape of the clipping plane in the three-dimensional region of interest to which the rendering is applied can be set independently and quickly, to enable reduction of the load of the user during operation and shortening of the examination time.

According to one aspect of the present invention, there is provided an ultrasonic volume data processing device comprising a three-dimensional region-of-interest setting unit which sets a three-dimensional region of interest for a rendering process with respect to ultrasonic volume data obtained from a three-dimensional space in a living body, and a three-dimensional ultrasonic image forming unit which executes the rendering process using data in the three-dimensional region of interest, to form a three-dimensional ultrasonic image, wherein the three-dimensional region of interest has a clipping plane which spatially separates a target tissue and a non-target tissue, and the three-dimensional region-of-interest setting unit comprises a deformation unit which deforms the clipping plane and an inclination unit which causes the entirety of the clipping plane to be inclined.

In the above-described configuration, the ultrasonic volume data are obtained by transmission and reception of ultrasound to and from a three-dimensional space in a living body. The three-dimensional region-of-interest setting unit sets a virtual three-dimensional region of interest with respect to the ultrasonic volume data. The three-dimensional region of interest is a partial region in which the rendering process is applied. The rendering process is desirably a process based on the volume rendering, but may be any of other processes. The three-dimensional region of interest has a clipping plane which functions as a separating surface or a boundary surface. The clipping plane is in particular a rendering start surface, but may be any of other surfaces. In any case, the clipping plane is a surface targeted to spatially separate the target tissue for which an image is to be formed and a non-target tissue for which the image is not to be formed. The three-dimensional region-of-interest setting unit comprises a deformation unit and an inclination unit, which are desirably realized as functions of software. The deformation unit deforms the shape of the clipping plane. In this case, the clipping plane may be deformed by moving one or a plurality of representative points through which the clipping plane passes. Preferably, the shape of the clipping plane is determined by a height position of a representative point. The inclination unit causes the entire clipping plane to be inclined after or before deformation of the clipping plane. There may be employed a structure which can cause the clipping plane to de inclined only in a first direction, but preferably, there is employed a structure which causes the clipping plane to be inclined in both a first direction and a second direction. In either case, if the entire clipping plane can be inclined, the clipping plane can be inclined to match the inclination direction of the gap between tissues in a state where two tissue surfaces oppose each other. When, for example, the clipping plane has four corners, the heights of the four corners can be arbitrarily set according to the two-dimensional inclination of the clipping plane. The clipping plane may be deformed and then inclined, or the clipping plane may be inclined and then deformed. Alternatively, there may be employed a configuration which allows simultaneous or alternate deformation and inclination, in a free manner. When it becomes necessary to correct the size by the inclination of the clipping plane, an enlarging process (or reducing process) is applied to the clipping plane.

According to the above-described configuration, there can be obtained an advantage that the clipping plane can be set easily and quickly between a target tissue and a non-target tissue in a living body. In particular, because the shape of the clipping plane can be set to a suitable shape, and, at the same time, the orientation of the clipping plane can be set to a suitable orientation, the quality of the rendering process result can be improved. For example, when a three-dimensional image of the fetus is formed, it is possible to easily avoid a problem such as that the face of the fetus is hidden behind the placenta. The ultrasonic volume data processing device may be formed with an ultrasonic diagnosis apparatus, by a computer which processes data obtained by the ultrasonic diagnosis apparatus, or by another device.

According to another aspect of the present invention, it is desirable that, in the ultrasonic volume data processing device, the deformation unit deforms the clipping plane into a convex shape or a concave shape. As, based on experience, the shape of the gap between tissues is in many cases a concave surface or a convex surface, it is desirable to enable selection of both the convex shape and the concave shape as the shape of the clipping plane. Alternatively, it is also possible to employ as the clipping plane a surface having a complex shape with a plurality of depressions and projections. However, in consideration of the operability of the user, it is preferable to employ a structure which allows quick designation of a simple convex clipping plane or concave clipping plane by moving in a vertical direction a representative point at the center.

According to another aspect of the present invention, it is preferable that, in the ultrasonic volume data processing device, the clipping plane has a first horizontal direction, a second horizontal direction, and a vertical direction as three directions of inclination movement, and the deformation unit determines a height in the vertical direction for a representative point of the clipping plane according to a parameter h designated by a user. The three directions move while maintaining an orthogonal relationship. The vertical direction corresponds to a direction of normal, and, with setting of the height of the representative point in the vertical direction, the deformation direction and radius of curvature of the clipping plane can be freely set.

According to another aspect of the present invention, it is desirable that, in the ultrasonic volume data processing device, shapes on both sides of the representative point are in a line symmetric relationship in the first horizontal direction, and shapes on both sides of the representative point are in a line symmetric relationship in the second horizontal direction. With such a symmetry, it is possible to allow the user to intuitively and easily recognize the three-dimensional region of interest.

According to another aspect of the present invention, it is preferable that, in the ultrasonic volume data processing device, the inclination unit determines a two-dimensional inclination orientation of the clipping plane according to a first inclination angle $\theta 1$ and a second inclination angle $\theta 2$. By allowing independent setting of the inclination angles in two directions, it is possible to accurately match the clipping plane in a direction of existence of the gap between tissues.

According to another aspect of the present invention, it is preferable that the ultrasonic volume data processing device further comprises a size adjustment unit which adjusts a size of the clipping plane according to an inclination angle of the clipping plane. When the clipping plane is inclined, a projected figure of the clipping plane may not match the projected figure of the three-dimensional region of interest, resulting in occurrence of a spatial deviation between the projected figures. In consideration of this, the sizes of the projected figure can be matched by executing size adjustment of the clipping plane (in particular, an enlargement process). With this configuration, a normal three-dimensional shape can be maintained. In place of the size adjustment of the clipping plane, it is also possible to execute size adjustment of the region of interest itself. In addition to the enlargement correction, a reduction correction may be employed.

According to another aspect of the present invention, it is preferable that, in the ultrasonic volume data processing device, the size adjustment unit increases the size of the clipping plane as the inclination angle of the clipping plane is increased. In this case, it is desirable to employ a configuration such that the size of the clipping plane is changed while maintaining similarity in shape.

According to another aspect of the present invention, it is preferable that, in the ultrasonic volume data processing device, in a first step, the deformation unit creates a clipping plane after deformation; in a second step after the first step, the inclination unit causes the clipping plane after deformation to be inclined, to create a clipping plane after deformation and inclination; and, in a third step after the second step, the size adjustment unit adjusts the size of the clipping plane after deformation and inclination, to create a clipping plane after deformation, inclination, and size adjustment. With such a configuration, calculation can be simplified, and a software process can be executed quickly.

According to another aspect of the present invention, it is preferable that, in the ultrasonic volume data processing device, the deformation unit creates first three-dimensional shape data as the clipping plane after deformation, the inclination unit creates second three-dimensional shape data as the clipping plane after deformation and inclination by a rotational conversion of the first three-dimensional shape data, the size adjustment unit creates third three-dimensional shape data as the clipping plane after deformation, inclination, and size adjustment by an enlargement conversion of the second three-dimensional shape data, and a voxel calculation start point on each ray when the rendering process is executed is defined based on the third three-dimensional shape data. The clipping plane may be represented by a function, rather than with spatially distributed points.

According to another aspect of the present invention, it is preferable that the ultrasonic volume data processing device further comprises a tomographic image forming unit which forms a first tomographic image and a second tomographic image which are orthogonal to each other, based on the ultrasonic volume data; a graphic image forming unit which forms a first graphic image and a second graphic image representing two cross sections of the three-dimensional region of interest which are orthogonal to each other; and a display unit which displays a first display image in which the first graphic image is combined over the first tomographic image and displays a second display image in which the second graphic image is combined over the second tomographic image, wherein, when the three-dimensional region of interest is changed, contents of the first graphic image and the second graphic image are changed in connection with the change of the three-dimensional region of interest. The user can recognize the position, shape, or the like of the three-dimensional region of interest through such first display image and second display image.

According to another aspect of the present invention, it is preferable that the ultrasonic volume data processing device further comprises a storage unit which stores a plurality of initial parameter sets, and a selection unit which selects a particular parameter set from the plurality of initial parameter sets, wherein the three-dimensional region-of-interest setting unit sets an initial three-dimensional region of interest according to the particular parameter set. By preparing in advance a plurality of initial parameter sets corresponding to a plurality of initial shapes, it is possible to quickly set a desired three-dimensional region of interest, and the load imposed on the user in such a case can be reduced. It is preferable to configure the device such that a parameter set defining a three-dimensional region of interest which has been set in the past can be additionally registered and used at a later time.

(2) Solution to Second Problem

A second advantage of the present invention is that a striped pattern formed on the three-dimensional image is reduced or resolved.

According to one aspect of the present invention, there is provided an ultrasonic volume data processing device comprising a three-dimensional region-of-interest setting unit which sets a three-dimensional region of interest in which a rendering process is applied, with respect to ultrasonic volume data, and a three-dimensional ultrasonic image forming unit which forms a three-dimensional ultrasonic image by setting a plurality of rays for the three-dimensional region of interest and repeatedly executing a voxel calculation along each ray, wherein the plurality of voxel calculations for each ray include a special voxel calculation for inhibiting formation of a striped pattern caused by at least one of a start surface and an end surface in the three-dimensional region of interest being curved.

According to the above-described configuration, in a case where a rendering process is executed using a three-dimensional region of interest, even when one of the rendering start surface and the rendering end surface in the three-dimensional region of interest is curved, because a special voxel calculation for inhibiting the formation of the striped pattern is executed, when the three-dimensional image is displayed, the striped pattern is not formed or, even if the striped pattern is formed, the striped pattern does not become notable. With such a configuration, it is possible to improve the quality of the three-dimensional image. The above-described special process can be applied when at least one of the rendering start surface and the rendering end surface in the three-dimensional region of interest is non-planar or when the path lengths of the plurality of rays which are set in the three-dimensional region of interest vary along the direction of arrangement of the rays.

According to another aspect of the present invention, it is preferable that, in the ultrasonic volume data processing device, the special voxel calculation is a voxel calculation which uses a fraction of less than a certain sampling interval caused when a plurality of sampling points are set for each ray at the certain sampling interval. With this configuration, the non-uniformity among the rays can be recognized as the fraction, and a process for reducing the non-uniformity can be executed using the fraction.

According to another aspect of the present invention, it is preferable that, in the ultrasonic volume data processing device, the fraction corresponds to a distance between a voxel which is one voxel before the end surface, and the end surface. According to another aspect of the present invention, it is preferable that, in the ultrasonic volume data processing device, the special voxel calculation is a voxel calculation for an end voxel determined based on the end surface and in which the distance acts as a weight value. According to another aspect of the present invention, it is preferable that, in the ultrasonic volume data processing device, the end voxel is a voxel determined by the certain sampling interval. According to another aspect of the present invention, it is preferable that, in the ultrasonic volume data processing device, the end voxel is a voxel which is additionally set on the end surface and which is not determined by the certain sampling interval.

DESCRIPTION OF EMBODIMENTS

Preferred embodiments of the present invention will now be described with reference to the drawings.

(1) Setting of Three-Dimensional Region of Interest

Figure 1:
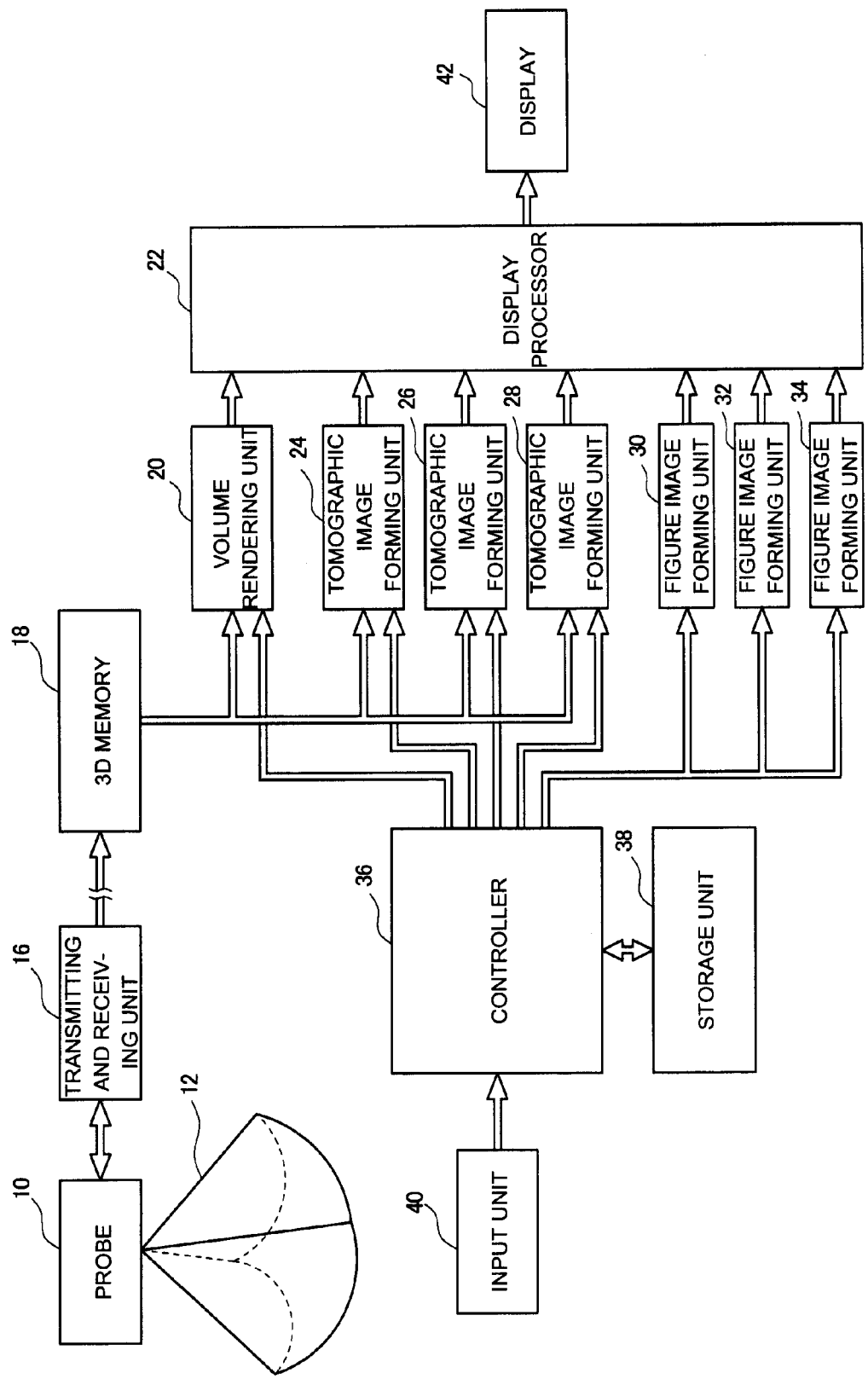
FIG. 1 is a block diagram showing the overall structure of an ultrasonic volume data processing device according to a preferred embodiment of the present invention.

FIG. 1 is a block diagram showing an ultrasonic diagnostic apparatus functioning as an ultrasonic volume data processing device. The ultrasonic diagnostic apparatus is used in the medical field, and has a function to form a three-dimensional image of a tissue within a living body by transmitting and receiving ultrasound. In the present embodiment, the target tissue for which an image is to be formed is a fetus. Alternatively, images of other tissues may be formed.

A probe 10 is a transmitting and receiving unit for capturing three-dimensional echo data. In the present embodiment, the probe 10 comprises a 1-D array transducer, and a scanning mechanism which mechanically scans the 1-D array transducer. An ultrasonic beam is formed by the 1-D array transducer, a scan plane is formed by electrical scanning of the ultrasonic beam, and a three-dimensional space 12 which is a three-dimensional echo data capturing space is formed by mechanically scanning the scan plane. Alternatively, a 2-D array transducer may be provided for the probe 10, and the ultrasonic beam may be two-dimensionally and electrically scanned. With such a structure also, the three-dimensional space 12 can be formed. As the electrical scan method, methods such as electrical sector scanning, electrical linear scanning, etc. are known. The probe 10 is brought into contact with a surface of a body. Alternatively, a probe which is inserted into a body cavity may be used. When an ultrasonic diagnosis of a fetus is executed, the probe 10 is brought into contact with a surface of a stomach portion of the mother, and the ultrasound is transmitted and received in this state.

A transmitting and receiving unit 16 functions as a transmission beam former and a reception beam former. Specifically, upon the transmission, a plurality of transmission signals are supplied from the transmitting and receiving unit 16 to the probe 10, and a transmission beam is formed. Upon the reception, a reflected wave from the living body is received by the probe 10, and a plurality of reception signals are output from the probe 10 to the transmitting and receiving unit 16. In the transmitting and receiving unit 16, a phase alignment and summation process for the plurality of reception signals is executed, and beam data are output as a reception signal after the phase alignment and summation. Various signal processes performed by signal processing modules (not shown) are applied to the beam data, and processed beam data are stored in a 3-D memory 18. One beam data set comprises a plurality of echo data sets aligned in the beam direction.

The 3-D memory 18 has a data space corresponding to the three-dimensional space 12. In the 3-D memory 18, volume data are stored as a collection of echo data obtained from the three-dimensional space 12. The volume data actually is formed by coordinate conversion and interpolation processes for the plurality of echo data sets. Alternatively, volume data comprising Doppler information may be formed. Alternatively, coordinate conversion for each echo data set may be executed not when the data are written but when the data are read.

A volume rendering unit 20 executes a rendering process using data within a three-dimensional region of interest according to rendering conditions given from a controller 36, to form a three-dimensional image. The image data is output to a display processor 22. Various methods are known as the volume rendering method, and these methods may be selectively used. Alternatively, other image processes such as surface rendering may be used in place of the volume rendering.

Tomographic image forming units 24, 26, and 28 are modules which form black-and-white B mode tomographic images. In the present embodiment, three tomographic images (triplane) corresponding to three cut surfaces passing through the center point (origin) of the three-dimensional region of interest are formed. Alternatively, the cut surfaces may be formed to be movable in an X direction, a Y direction, or a Z direction to be described later. The data of three tomographic images formed by the tomographic image forming units 24, 26, and 28 are output to the display processor 22. The conditions necessary for the image processing of the tomographic image forming units 24, 26, and 28 are provided from the controller 36.

Figure image forming units 30, 32, and 34 are modules which form graphic images displayed in an overlaid manner on the three tomographic images. In the present embodiment, the figure image forming unit 30 forms a graphic image representing a YX cross section of the region of interest, and the figure image forming unit 32 forms a graphic image representing a YZ cross section of the three-dimensional region of interest. The figure image forming unit 34 forms a graphic image representing the other cross sectional shape of the three-dimensional region of interest. The images thus formed are output to the display processor 22. Conditions and data necessary for image formation by the figure image forming units 30, 32, and 34 are provided from the controller 36.

The display processor 22 comprises an image-combining function, forms a display image based on the plurality of input images, and outputs data representing the display image to a display 42. An example of images to be displayed on the display 42 will be described later with reference to FIG. 2.

In the present embodiment, the controller 36 is formed from a CPU and an operation program. The volume rendering unit 20, the tomographic image forming units 24, 26, and 28, and the figure image forming units 30, 32, and 34 are realized as functions of software. A storage unit 38 is connected to the controller 36, and an input unit 40 is connected to the controller 36. In the present embodiment the input unit 40 is formed from an operation panel, and the operation panel comprises a keyboard, a trackball, etc. The user can use the input unit 40 to input necessary numerical values for setting the three-dimensional region of interest. The storage unit 38 stores, in advance, a plurality of parameter sets, which will be described later with reference to FIG. 4. In addition, a work area is secured in the storage unit 38, and shape data representing the clipping plane are stored in the work area as necessary. In the present embodiment, the controller 36 has a setting function of the three-dimensional region of interest. This function will be described later with reference to FIGS. 5-12.

Figure 2:
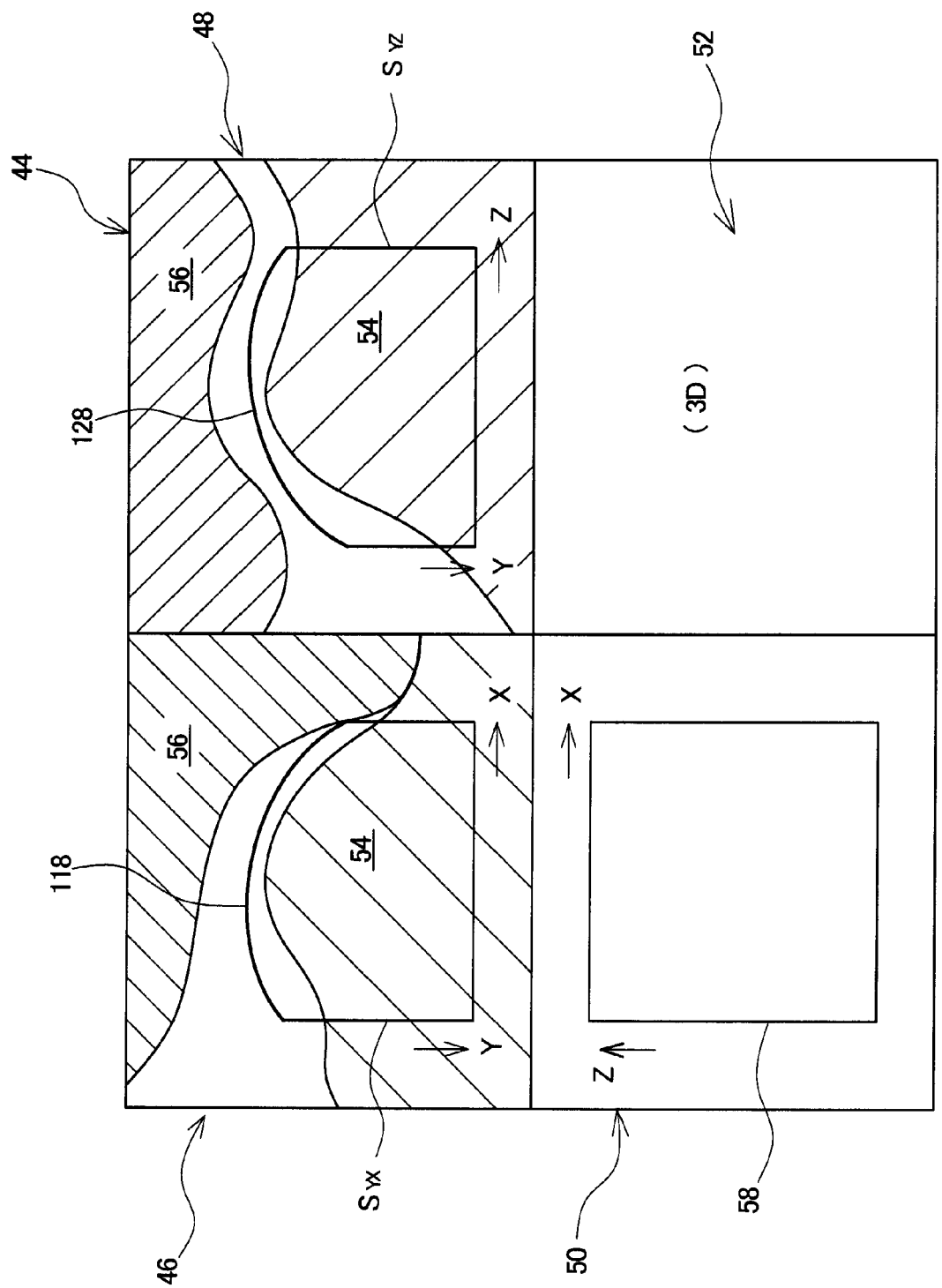
FIG. 2 is a diagram exemplifying an image displayed on a display.

FIG. 2 shows an example of an image displayed on the display. Reference numeral 44 represents a display image. The display image 44 includes three tomographic images 46, 48, and 50, and further includes a three-dimensional image 52. The three tomographic images 46, 48, and 50 are in orthogonal relationship to each other, and form the triplane as a whole. More specifically, the tomographic image 46 is a tomographic image representing the YX cross section, and a cross sectional shape $S_{YX}$ as a graphic image is included in the tomographic image 46. The cross sectional shape $S_{YX}$ represents the YX cross section of the three-dimensional region of interest, and includes a curve 118 representing a cross section of the clipping plane. Reference numeral 54 represents a tissue for which an image is to be formed, and reference numeral 56 represents a tissue for which an image is not to be formed. The curve 118 is curved and inclined along a gap between the tissue 54 and the tissue 56.

The tomographic image 48 includes a cross sectional shape $S_{YZ}$ representing the YZ cross section of the three-dimensional region of interest and includes a curve 128 representing the YZ cross section of the clipping plane. The curve 128 is inclined and curved along a gap between the tissue 54 for which an image is to be formed and the tissue 56 for which an image is not to be formed, and spatially separates these two tissues. Alternatively, in place of the curves 118 and 128 having a convex shape, curves 118 and 128 having a concave shape may be set.

In the tomographic image 50, a cross sectional shape 58 of a quadrangle shape representing the XZ cross section of the three-dimensional region of interest is represented. The position and size of the three-dimensional region of interest can be arbitrarily changed by the user. As will be described in detail later, the shape and orientation of the clipping plane can be arbitrarily set by the user.

The three-dimensional image 52 is an image formed using data belonging to the three-dimensional region of interest which is set as described above. In the present embodiment, as will be described below with reference to FIG. 3, the clipping plane corresponds to the rendering start surface, and a plurality of rays are set in parallel to each other along the Y direction. The viewpoint is at an upper part in the Y direction (on a side of the origin). In the rendering process, a plurality of voxel data sets are sampled on each ray. Each voxel data set is formed by referring to a plurality of actual data sets existing around sample points and through interpolation. When the interpolation process is executed, data outside of the three-dimensional region of interest may be referred to.

Figure 3:
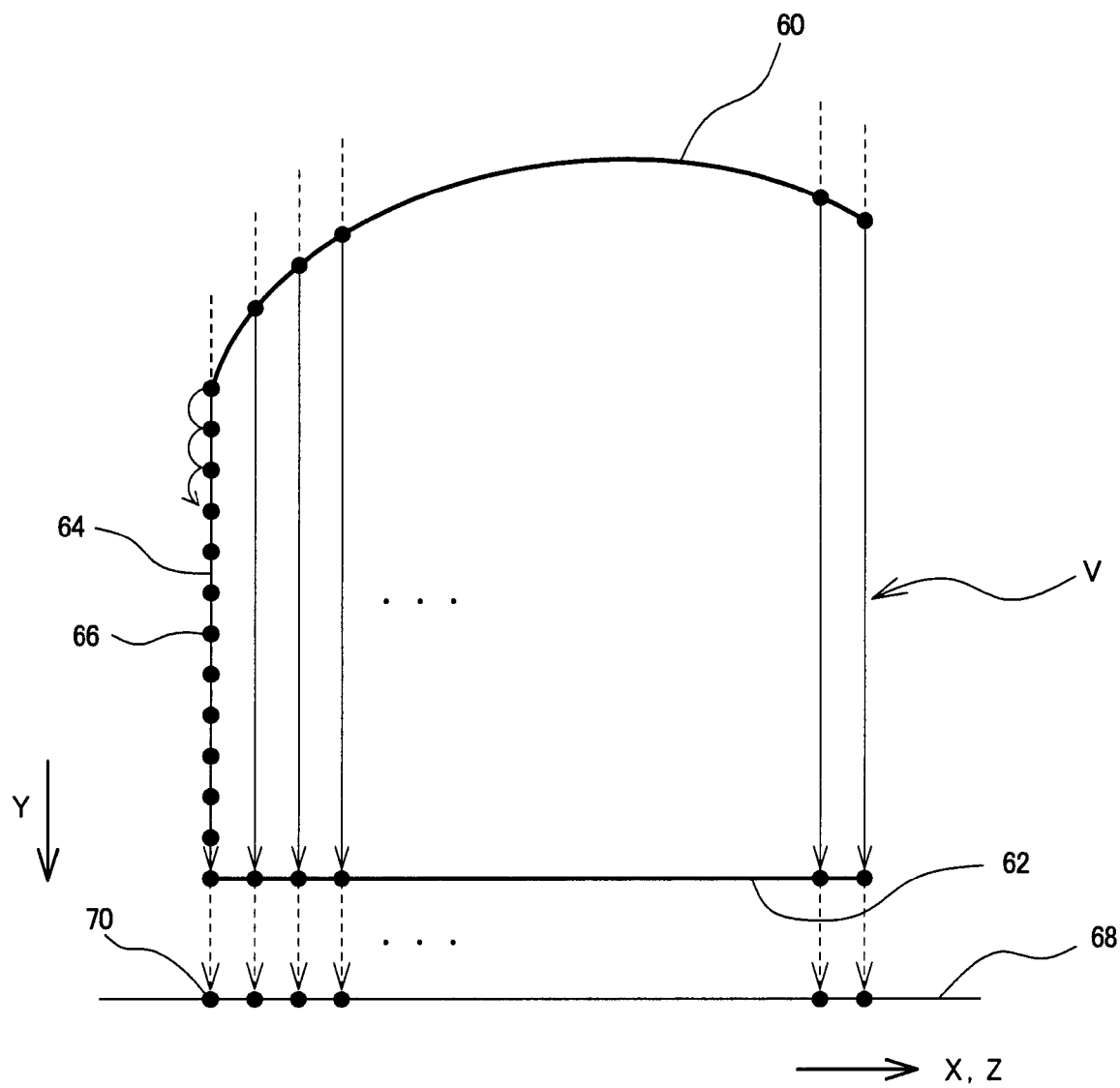
FIG. 3 is a diagram for explaining a rendering process using a three-dimensional region of interest.

FIG. 3 shows a rendering process using the three-dimensional region of interest as a conceptual view. For a three-dimensional region of interest V, a plurality of rays 64 are set in parallel to each other along the Y direction. The configuration is not limited to parallel projection, and other projection methods may be applied. A clipping plane 60 in the three-dimensional region of interest V can be deformed and inclined in the present embodiment. The clipping plane 60 corresponds to the rendering start surface, as already described. The surface on the side opposite the clipping plane 60 is an end surface 62, which is represented as a bottom plane in FIG. 3. On each ray, voxel calculation is successively executed with a predetermined sampling interval. For each voxel, an amount of output light is calculated based on an amount of input light, and, in this case, opacity (degree of unclearness or non-transparency) serves as a parameter. When the voxel calculation is successively proceeded for each ray and reaches the end surface 62, the voxel calculation on that ray is completed. Alternatively, when the amount of output light calculated for each voxel reaches a maximum value (for example, 1.0), the voxel calculation is completed. The amount of output light at the time of completion of the voxel calculation becomes the pixel value. In other words, the pixel value of a pixel 70 corresponding to a ray 64 on a virtual screen 68 is determined as a final amount of output light determined for the ray 64. As a result of similar processes for the plurality of rays, a three-dimensional image is constructed on the screen 68.

Figure 4:
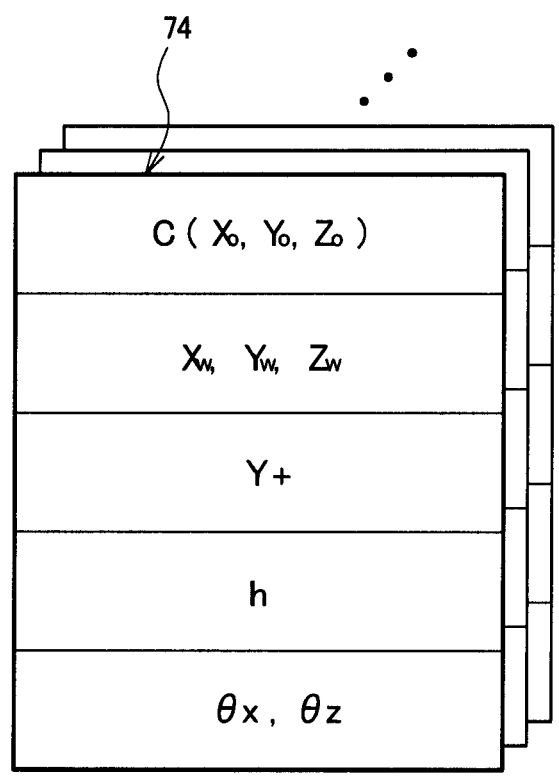
FIG. 4 is a diagram showing a plurality of parameter sets stored in a storage unit.

FIG. 4 shows a plurality of parameter sets stored in the storage unit shown in FIG. 1. When one of the parameter sets, parameter set 74, is considered, the parameter set 74 includes a coordinate $(X_0, Y_0, Z_0)$ of the origin C of the three-dimensional region of interest, a size $(X_W, Y_W, Z_W)$ of the three-dimensional region of interest, an amount of offset in the Y direction $(Y_+)$, a height h of the clipping plane, and inclination angles $\theta_X$ and $\theta_Z$ of the clipping plane. The configuration shown in FIG. 4 is merely exemplary, and other configurations may be employed. In the present embodiment, for example, 8 initial shapes are determined as the three-dimensional region of interest, and 8 parameter sets 74 corresponding to the 8 initial shapes are registered in the storage unit. Therefore, the user can instantaneously set a three-dimensional region of interest having a desired initial shape by selecting a parameter set, and may apply a necessary modification. Alternatively, the parameter set representing the modified three-dimensional region of interest may be additionally registered in the storage unit.

Figure 5:
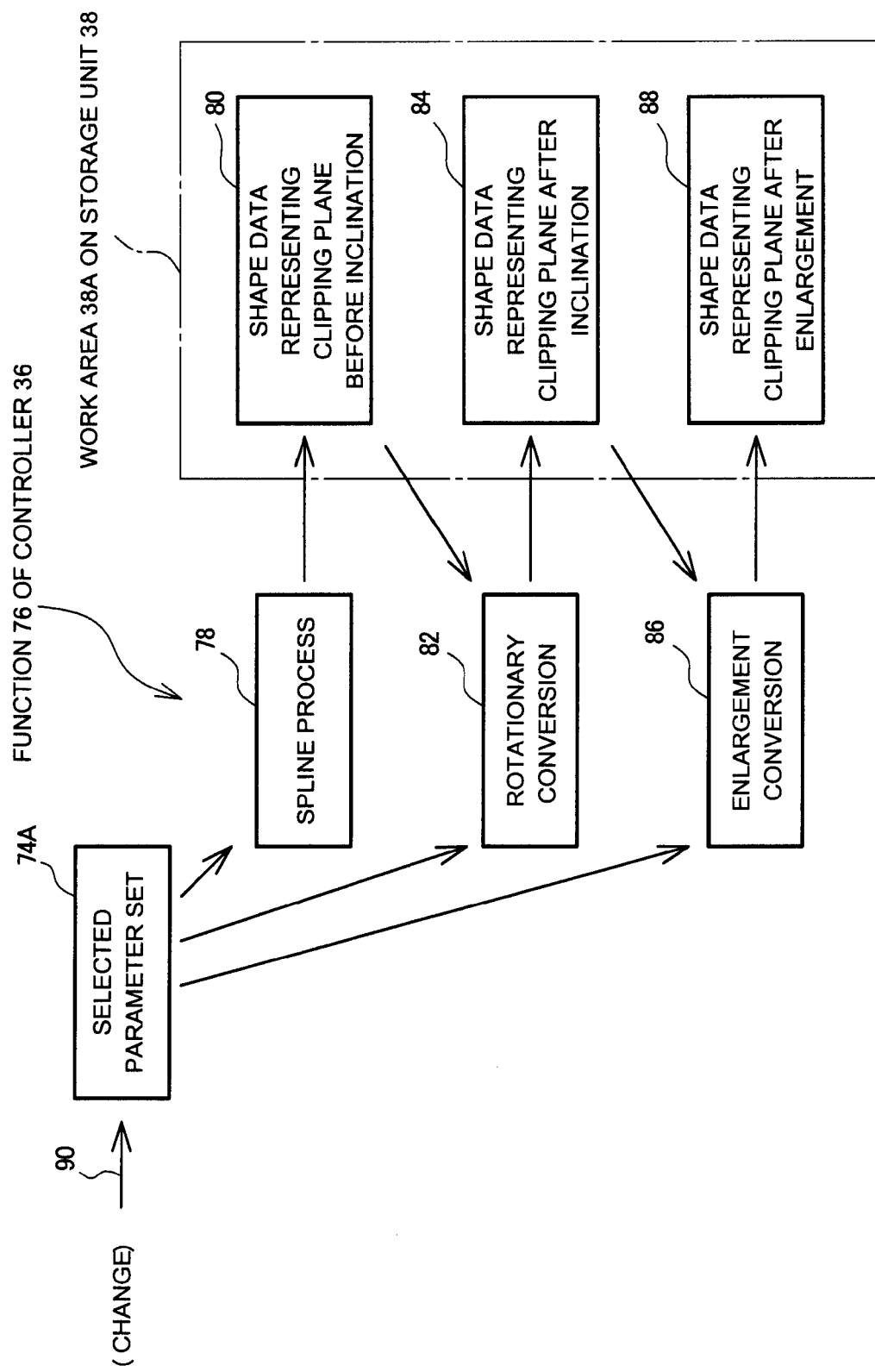
FIG. 5 is a conceptual diagram for explaining a creation process of a three-dimensional region of interest.

FIG. 5 shows a flow of the process related to the formation of the clipping plane as a conceptual diagram. Reference numeral 76 represents a function of the controller 36, and reference numeral 38A represents a work area on the storage unit 38. Reference numeral 74A represents a parameter set selected by the user. The parameters of the parameter set 74A can be arbitrarily changed by the user as shown by reference numeral 90. At a first stage, the parameter set 74A is referred to, and, by a spline process shown with reference numeral 78, a deformed clipping plane is formed. A normal line of the clipping plane is not inclined. That is, the clipping plane at this stage is a clipping plane before inclination. Specific examples of the clipping plane at this stage will be described in detail later with reference to FIG. 6 or the like. The clipping plane before inclination and after deformation created by the spline process 78 is actually created as three-dimensional shape data, and the three-dimensional shape data are temporarily stored in the work area 38A. The shape data are represented with reference numeral 80.

At a second stage, a rotational conversion process 82 is executed. More specifically, based on the parameter set 74A, the two-dimensional rotational conversion process 82 is applied to the shape data 80, and shape data 84 representing the clipping plane after inclination are created and stored in the work area 38A. The shape data 84 are transient data.

At a third stage, an enlargement conversion process 86 is applied to the shape data 84. With the enlargement conversion process 86, shape data 88 representing the clipping plane after enlargement are created, and are stored in the work area 38A. With the enlargement conversion process 86, the clipping plane to be actually functioned is established. In other words, the creation of the three-dimensional region of interest is completed. When any of the parameters is changed by the user as shown by reference numeral 90, the processes from the first stage to the third stage are executed again, with the change of the parameter as a trigger, and the three-dimensional region of interest is instantaneously updated.

Next, a creation process of the three-dimensional region of interest will be described in more detail with reference to FIGS. 6-9.

Figure 6:
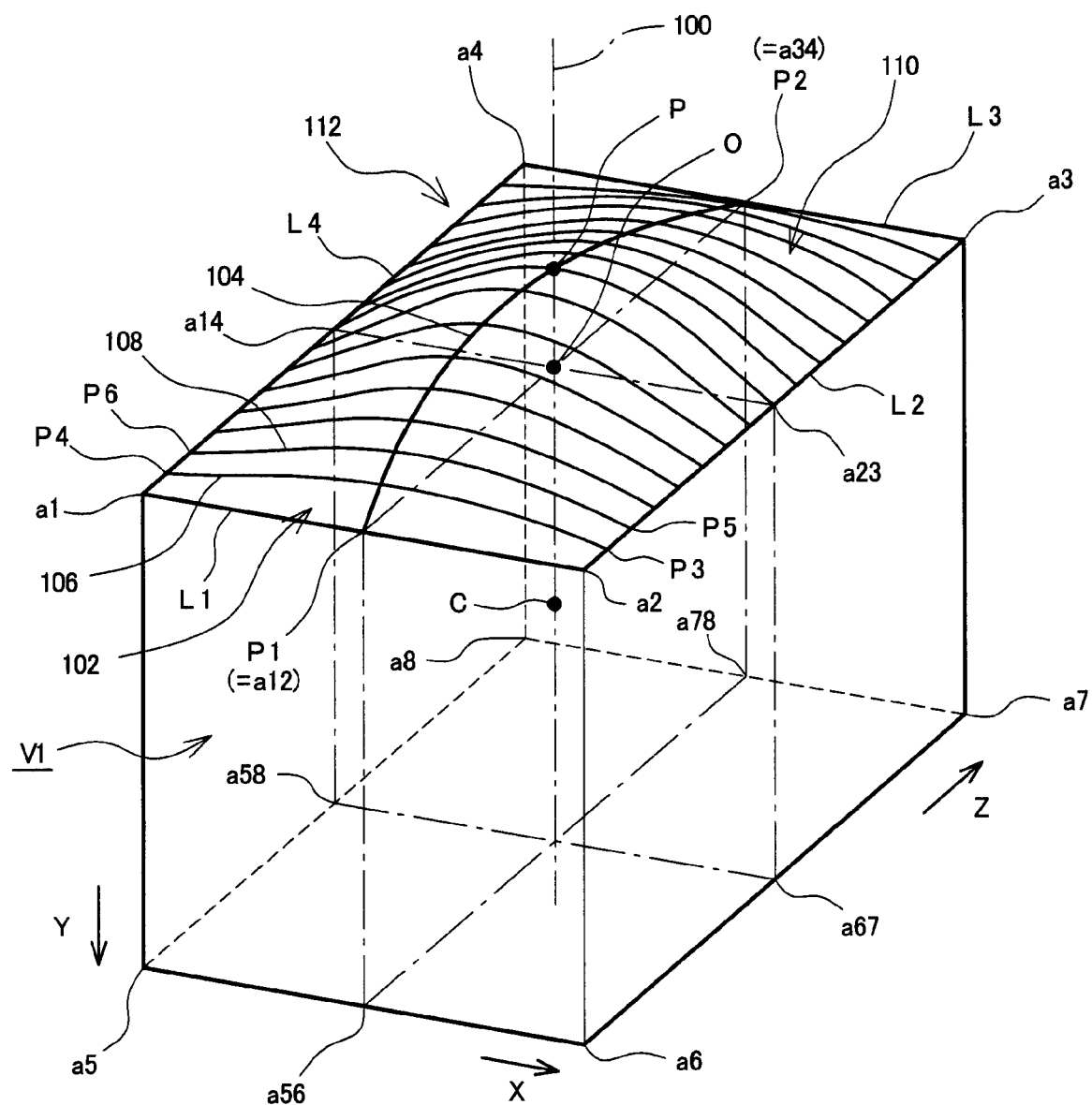
FIG. 6 is a conceptual diagram showing a clipping plane after deformation.

FIG. 6 shows a three-dimensional region of interest V1 at an initial state. The three-dimensional region of interest V1 is a region which virtually exists in a data process space. That is, the body portion other than the clipping plane 112 to be described below exists only as a numerical condition of the rendering process range, and no actual three-dimensional image is present. For the explanation of the present embodiment, however, in order to facilitate understanding of the technical content, the three-dimensional region of interest is represented as a figure that can be visually recognized. Alternatively, all of the three-dimensional region of interest may be created as a three-dimensional figure (or graphic data).

The three-dimensional region of interest V1 has an origin C, and a spatial position of the origin C is determined by an origin coordinate $(X_0, Y_0, Z_0)$ included in the above-described parameter set. The sizes of the three-dimensional region of interest V1 in the X direction, Y direction, and Z direction are determined by size information $(X_W, Y_W, Z_W)$ included in the above-described parameter set 74. The size information may define the overall width in the respective directions or a half width thereof. In FIG. 6, O represents a reference point, which is a point on a center line 100. The reference point O is a rotational center (fixed point) when the clipping plane 112 is inclined, as will be described later. When it is desired to adjust only the height of the reference point in the Y direction without affecting the size in the Y direction, a value of the offset value $Y_+$ may be changed. With the change of the value, the size on the upper side can be freely changed while maintaining the origin C. A height h is defined as a distance from the origin O along the center line 100. A point which is distanced from the reference point O by a distance h is a representative point P. When the parameter h has a positive value, the representative point P is positioned above the reference point O and, on the other hand, when the parameter h has a negative value, the representative point P is positioned below the reference point O.

In FIG. 6, 8 corners of the three-dimensional region of interest V1 are represented by a1, a2, a3, a4, a5, a6, a7, and a8. The middle points of the sides are represented by a12, a23, a34, a14, a56, a67, a78, and a58.

Creation of the clipping plane 112 will now be described in detail. When the representative point P is determined by the parameter h as described above, a curve 104 is created as a basic line similar to a backbone, through a spline interpolation calculation based on the representative point P and two endpoints P1 and P2. The end point P1 is the point a12 described above and the end point P2 is the point a34 described above. The curve 104 has a shape which is line symmetric in the Z direction with a representative point P therebetween.

When the curve 104 is determined as described above, a plurality of spline curves 106 and 108 are sequentially created between a side L1 and a side L3. More specifically, a plurality of end points P3, P4, P5, and P6 are determined in equal spacing for a side L2 and a side L4, and, similarly, a plurality of passing points are determined in the Z direction in equal spacing on the curve 104. For each position in the Z direction, the spline interpolation calculation is executed using the two end points and one passing point, to create a spline curve. In FIG. 6, a spline interpolation curve connecting the end points P3 and P4 is represented with reference numeral 106, and a spline interpolation curve connecting the end points P5 and P6 is represented with reference numeral 108. By creating such curves at respective positions in the Z direction, a curve array 110 can be formed, and, with the curve array 110, the clipping plane 112 at a state before inclination is constructed. The clipping plane 112 is in reality made of three-dimensional shape data. In the example configuration of FIG. 6, the plurality of spline interpolation curves are created aligned in the Z direction, but alternatively, the plurality of spline interpolation curves may be created aligned in the X direction.

Figure 7:
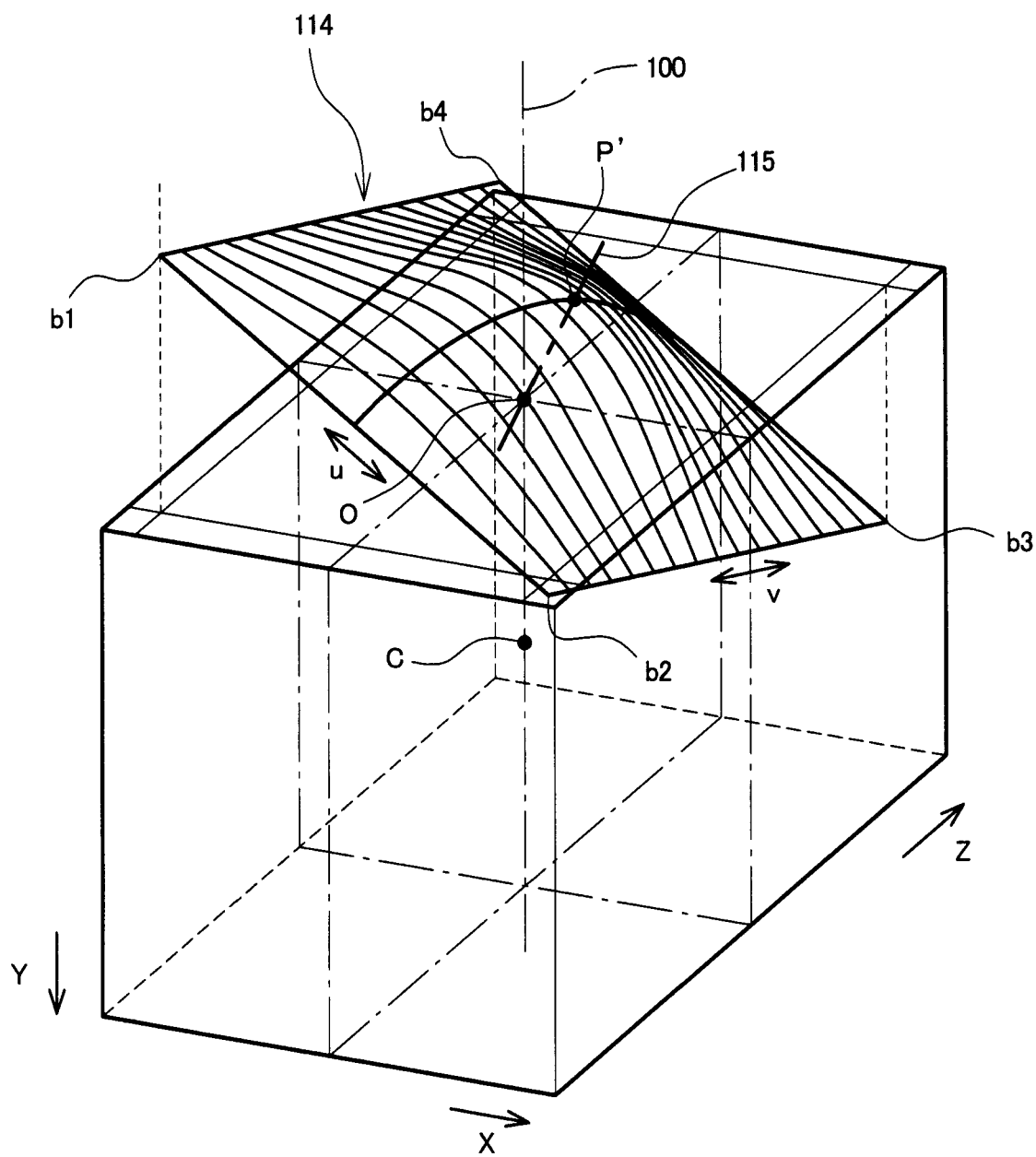
FIG. 7 is a conceptual diagram showing a clipping plane after deformation and inclination.

With the process of the first stage as described above, the clipping plane 112 which is not inclined is created. Next, as shown in FIG. 7, an inclined clipping plane 114 is created. More specifically, inclination angles $\theta_X$ and $\theta_Z$ forming a part of the parameter set are referred to, and the clipping plane is inclined in both the X direction and the Z direction. This process may be understood as inclination of a normal line 115, but the normal line itself is not calculated in the present embodiment. In order to facilitate understanding of the technical content, FIG. 7 shows a normal line. By the coordinate conversion of the three-dimensional shape data, the clipping plane after inclination 114 is constructed.

The normal line 115 is a line connecting the reference point O and a representative point after inclination P'. An inclination angle of the normal line 115 in the X direction is $\theta_X$ described above and an inclination angle of the normal line 115 in the Z direction is $\theta_Z$ described above. The clipping plane 114 has four corners b1, b2, b3, and b4. Because the clipping plane 112 shown in FIG. 6 is simply inclined, in the state shown in FIG. 7, the corners b1, b2, b3, and b4 are not on the 4 vertical sides and are positioned inside the 4 vertical sides. With such a configuration, the three-dimensional region of interest cannot be formed. In consideration of this, in the present embodiment, an enlargement process for creating a similar shape of the clipping plane 114 is executed. More specifically, the clipping plane 114 is enlarged in two horizontal directions including a u direction and a v direction, and at the same time the clipping plane 114 is also enlarged in the direction of the normal line 115 (vertical direction after inclination). The position of the reference point is not changed. The clipping plane after the enlargement is also constructed as three-dimensional shape data.

Figure 8:
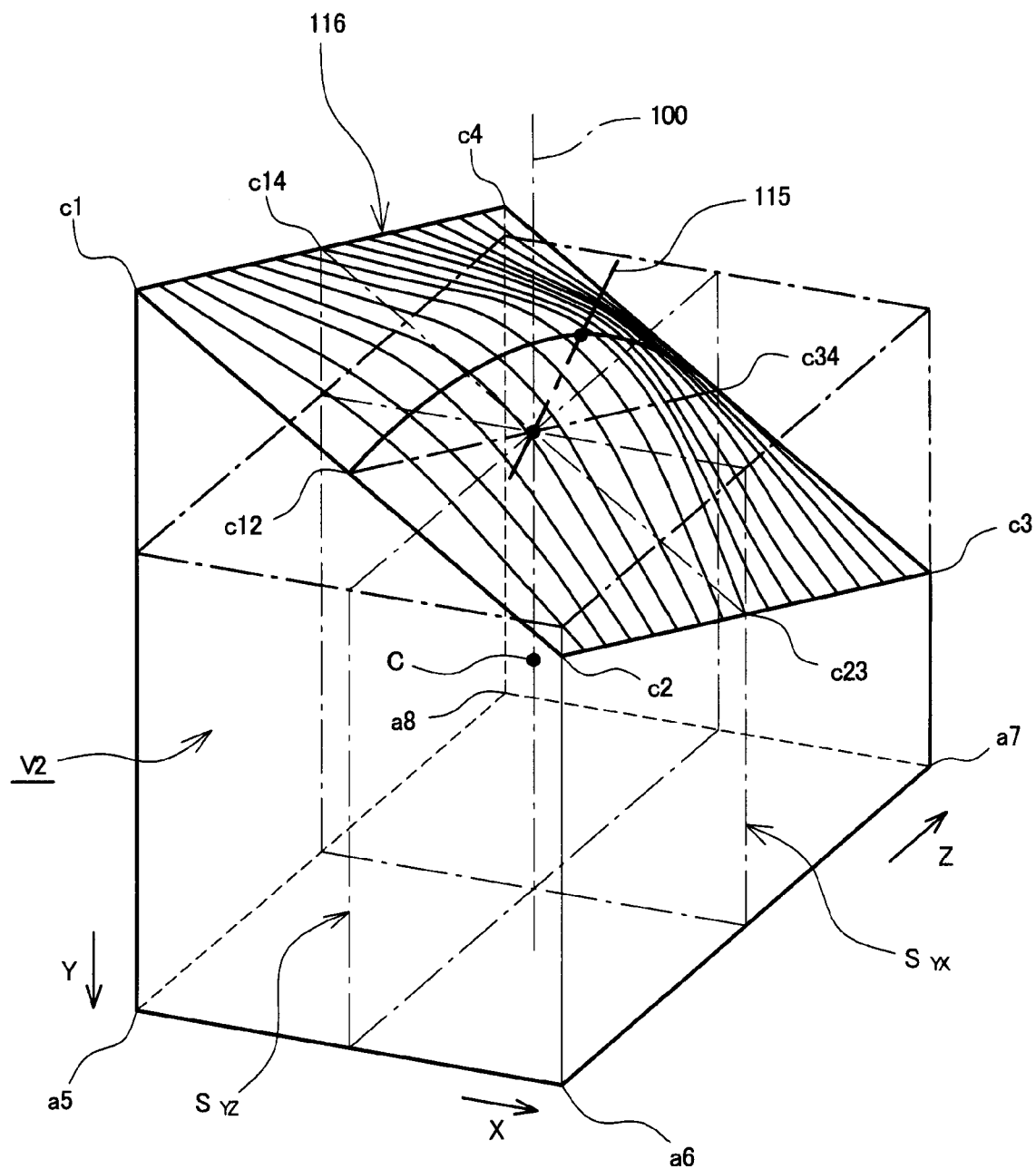
FIG. 8 is a conceptual diagram showing a clipping plane after deformation, inclination, and enlargement.

FIG. 8 shows a clipping plane 116 after enlargement. As a result of the enlargement process, 4 corners c1, c2, c3, and c4 are positioned on 4 vertical sides. With this configuration, a three-dimensional region of interest V2 including the clipping plane after inclination 116 is constructed. The three-dimensional region of interest V2 has a shape surrounded by 8 points c1, c2, c3, c4, a5, a6, a7, and a8. Meanwhile, in order to confirm the three-dimensional region of interest V2 on two tomographic images, cross sectional shape $S_{YX}$ and $S_{YZ}$ are created. In this case, a curve is created through spline interpolation calculation similar to that described above on a cross section connecting two end points c12 and c34, and, on a cross section orthogonal to this cross section also, the above-described curve is created through spline interpolation calculation between two endpoints c14 and c23. Creation of these cross sectional shapes will be described in more detail later with reference to FIGS. 10-12.

Figure 9:
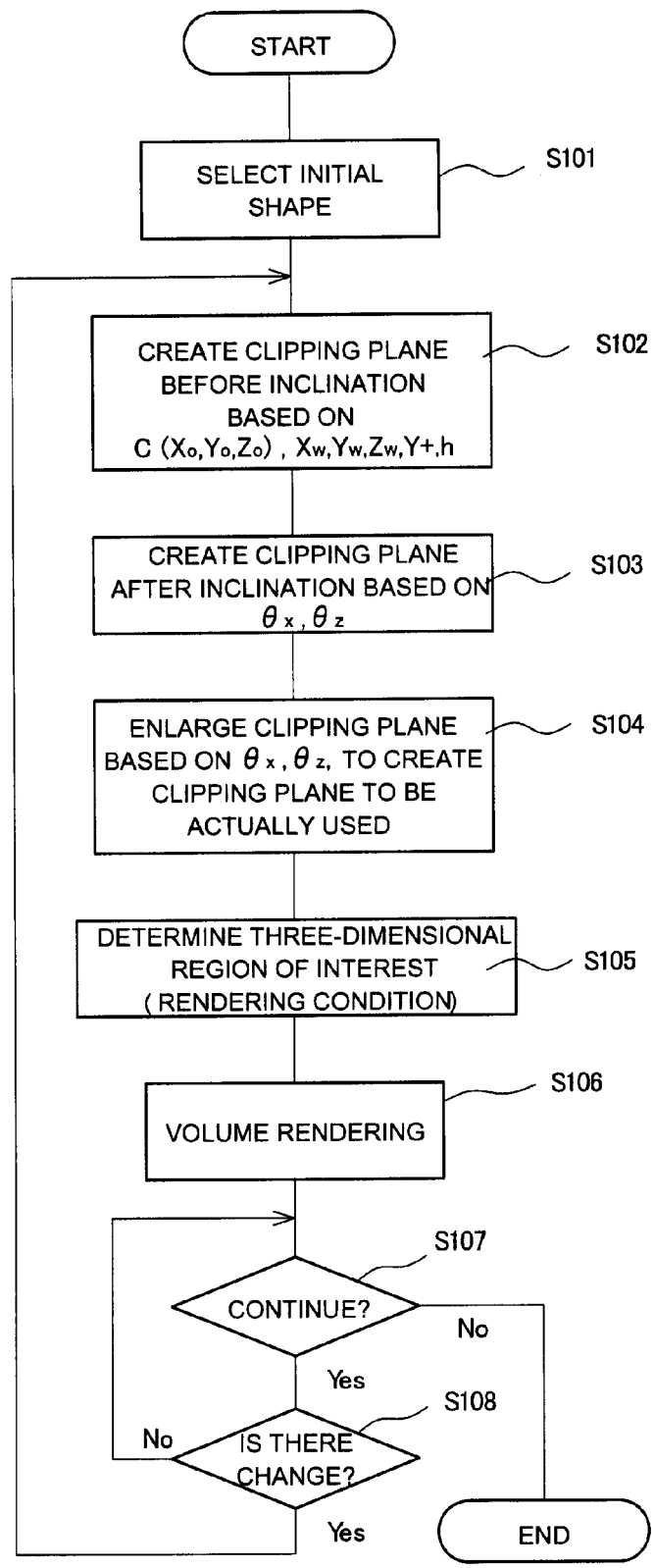
FIG. 9 is a flowchart for explaining a method of setting a three-dimensional region of interest.

FIG. 9 is a flowchart of a creation process of the three-dimensional region of interest described above. First, at S101, a user selects an initial shape to be actually used from among a plurality of initial shapes. More specifically, the parameter set corresponding to the initial shape selected by the user is recognized and referred to. In S102, a clipping plane before inclination is created based on an origin coordinate C ($X_0, Y_0, Z_0$) of the three-dimensional region of interest, size ($X_W, Y_W, Z_W$), offset $Y_+$, and height h of the clipping plane. In this creation process, the above-described spline interpolation calculation is executed. With this process, three-dimensional shape data representing the clipping plane is created. In S103, the clipping plane before inclination is spatially rotated based on the inclination angles $\theta_X$ and $\theta_Z$, to create the clipping plane after inclination. The clipping plane after inclination is also constructed with three-dimensional shape data. In S104, an enlargement process is applied to the clipping plane after inclination. In this case, a process for enlarging the shape while maintaining the similar shape as described above is executed. An enlargement percentage can be uniquely determined based on the inclination angles $\theta_X$ and $\theta_Z$. With the above-described processes, the clipping plane to be actually used is constructed as the three-dimensional shape data. In S105, a three-dimensional region of interest having the clipping plane constructed as described above is determined. The actual body of the three-dimensional region of interest actually includes three-dimensional shape data, and numerical value information defining a rendering range from the three-dimensional shape data. In S106, a volume rendering process is actually executed on the data in the three-dimensional region of interest. With this process, a three-dimensional image is formed, and the image data are displayed on the display screen. In S107, it is judged whether or not the above-described process is to be continued, and, when the above-described process is to be continued, it is judged in S108 whether or not there is a change for any of the parameters by the user. When it is judged that there is a change, the processes from S102 are repeatedly executed.

As described, according to the present embodiment, the clipping plane can be constructed as a simple convex plane or concave plane, and the clipping plane can be inclined in two directions. Therefore, even when the gap between the tissue for which an image is to be formed and the tissue for which an image is not to be formed is two-dimensionally inclined as shown in FIG. 2, the orientation of the clipping plane can be suitably set. In the present embodiment, because the shape of the clipping plane can be defined by defining only the height of the representative point forming the center point of the clipping plane, the process is easily understood by the user and confusion by the user can be prevented. It has been found through experimentation that, even when the clipping plane has a simple shape as described above, the matching of the clipping plane to the actual shape of the living body tissue is superior. In the present embodiment, the shapes on both sides of the representative point are in the line symmetric relationship in both the X direction and the Y direction, but alternatively, it is also possible to employ non-symmetric shapes on the respective sides of the representative point. Any of the 6 planes of a three-dimensional figure (a cube) may be employed as the clipping plane. It is desirable to employ a configuration such that the three-dimensional region of interest can be freely rotated with respect to the volume data.

Next, a creation method of the cross sectional shapes $S_{YX}$ and $S_{YZ}$ of the three-dimensional region of interest shown in FIG. 2 will be described with reference to FIGS. 10-12.

In the present embodiment, the creation of the three-dimensional region of interest and the creation of the cross-sectional shape of the three-dimensional region of interest are realized by calculation processes which are independent from each other. In FIG. 10, (A) shows a creation process of the cross sectional shape $S_{YX}$ and (B) shows a creation process of the cross sectional shape $S_{YZ}$.

In (A), an apparent representative point 210 is determined as follows. First, based on the height h on the center line 110, a curve along a depth direction (Z direction) is created through spline interpolation. The curve is rotated and enlarged based on the inclination angle $\theta_Z$. Then, on the resulting curve, a point of intersection with the center line 110 is identified. The intersection is the apparent representative point 210. This method, however, is merely an exemplary method. In (A), reference numeral 212 represents an initial curve. The initial curve 212 is created as a spline curve connecting the apparent representative point P10 and two end points a14 and a23. Various methods may be employed as the interpolation method for this purpose. The interpolation method to be used may be switched as necessary. Similar to the above-described creation process of the clipping plane, the rotational conversion is applied to the curve 212 based on the inclination angle $\theta_X$ in the X direction, and a curve after the rotation is represented by reference numeral 216. Two end points in the curve are shown with a14' and a23', and a representative point after movement is shown with P10$_X$. A straight line connecting the reference point O and the representative point after movement P10$_X$ is an apparent normal line 214. The representative point P10$_X$ and the normal line 14 are not actually calculated. A shape after an enlargement process is applied to the curve 216 is a curve 218. Two ends c14 and c23 thereof are positioned on left and right vertical sides. As a result of such a process, the YX cross section $S_{YX}$ of the three-dimensional region of interest is created as a box shape surrounded by 4 points c14, c23, a67, and a58. The YX cross section $S_{YX}$ is actually displayed over the tomographic image as a graphic image in an overlaid manner.

The YZ cross section $S_{YZ}$ is created in a similar manner. More specifically, in (B), a curve 222 is created through the spline interpolation calculation of 3 points P12, a12, and a34, and the curve 222 is rotationally converted based on the inclination angle $\theta_Z$ in the Z direction. The rotated curve is represented with reference numeral 226. A representative point P12$_Y$ is shown on an apparent normal line 224. The apparent normal line 224 and the representative point P12$_Y$ are not actually calculated. In (B), two end points a12' and a34' are deviated from the left and right vertical lines to the inside. A result of application of an enlargement process on the curve 226 is a curve 228. The two ends c14 and c23 thereof are positioned on the left and right vertical lines. With this process, the YZ cross sectional shape $S_{YZ}$ is created. The YZ cross sectional shape $S_{YZ}$ is displayed over the tomographic image in an overlaid manner.

Figure 10:
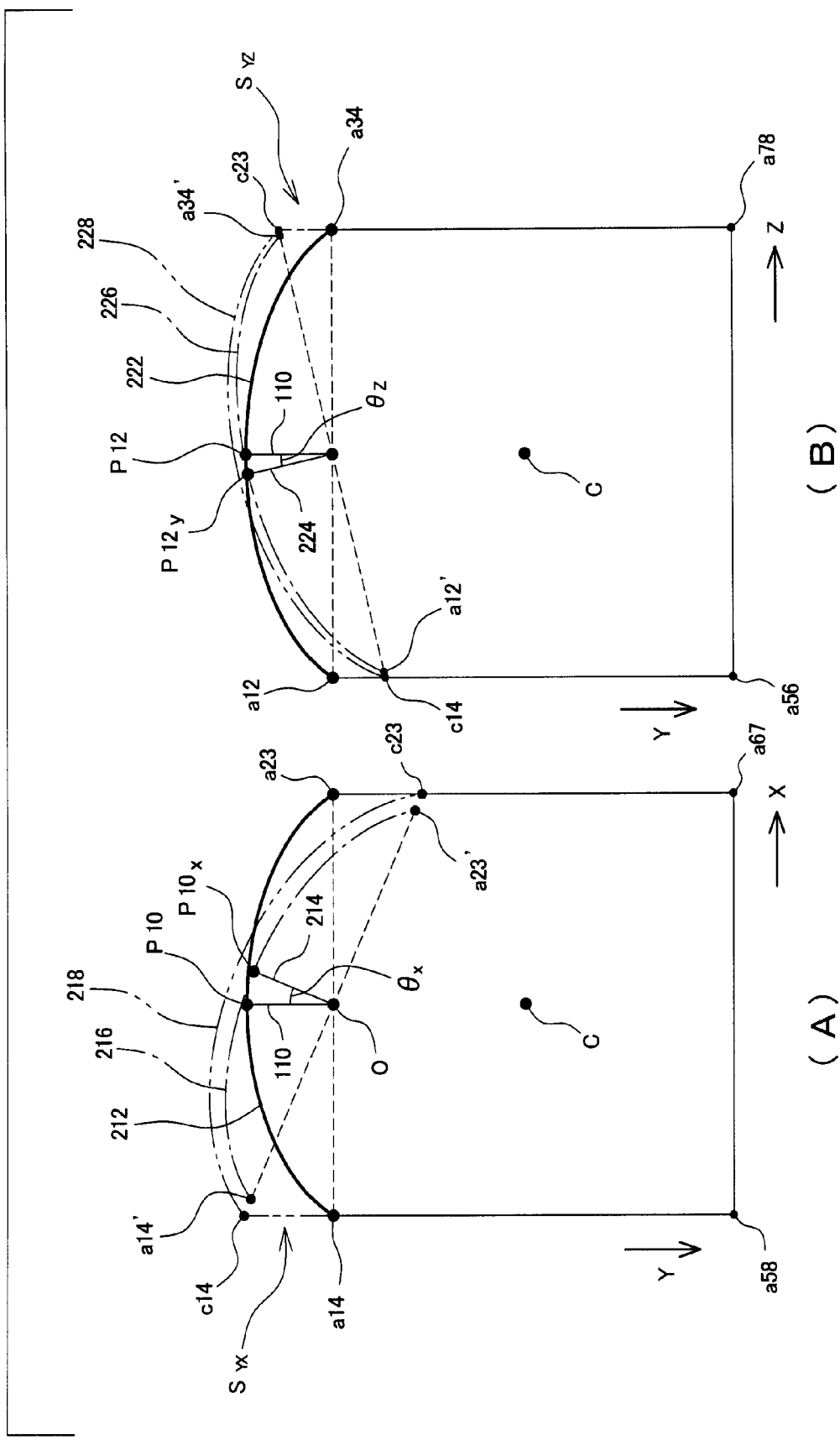
FIG. 10 is a diagram showing a YX cross sectional shape and a YZ cross sectional shape of the three-dimensional region of interest.
Figure 11:
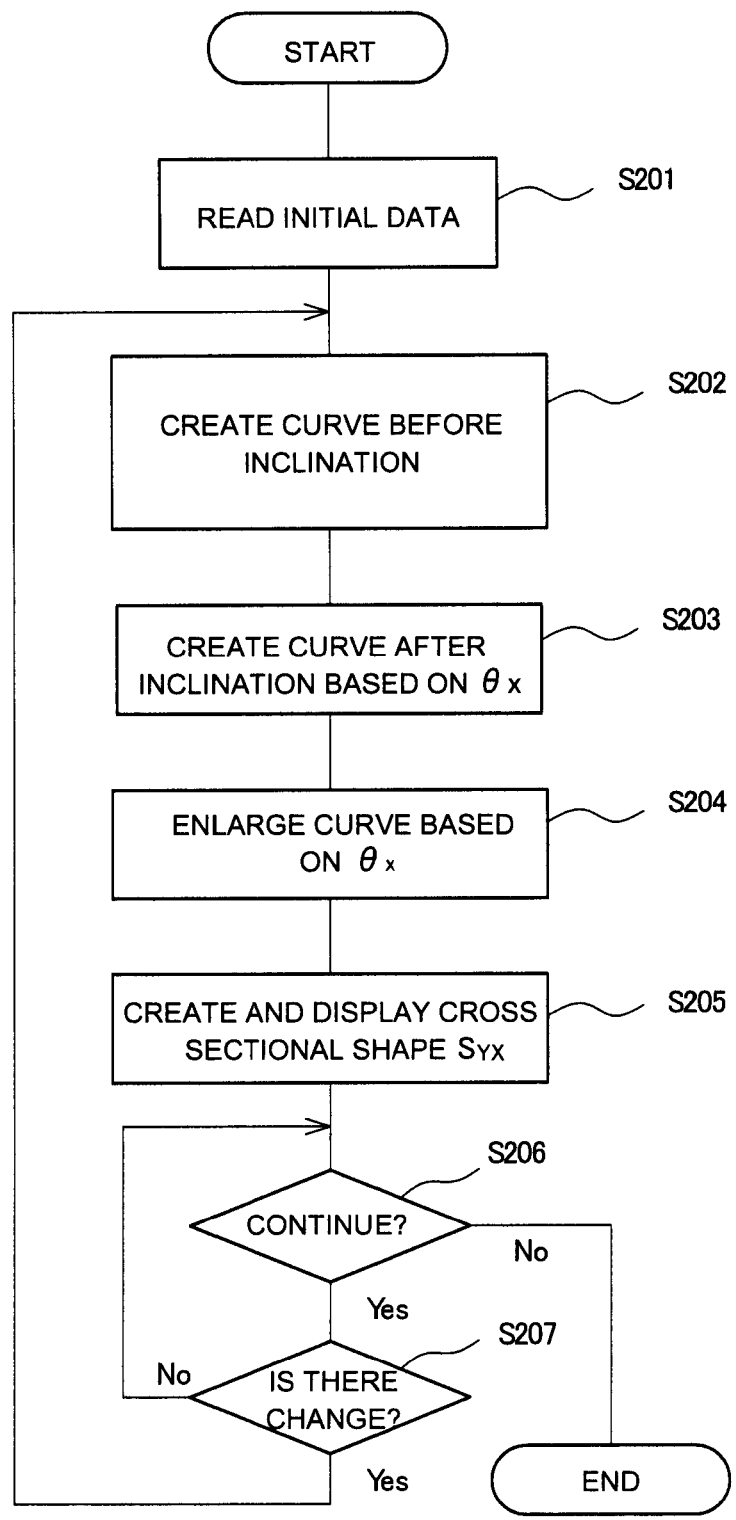
FIG. 11 is a flowchart showing a creation process of the YX cross sectional shape of the three-dimensional region of interest.

FIG. 11 is a flowchart of the creation process of the cross sectional shape $S_{YX}$ shown in (A) of FIG. 10. In S201, a parameter set selected by the user is referred to. In S202, a curve which is not inclined is created based on the selected parameter set. In S203, an inclined curve is created based on the inclination angle $\theta_X$ in the X direction. In S204, an enlargement process is applied on the curve after inclination based on the inclination angle $\theta_X$. In S205, a cross sectional shape $S_{YX}$ is determined as a box shape including the curve after the enlargement process, and is displayed on the tomographic image as a graphic. In S206, it is judged whether or not the above-described process is to be continued, and, if in S207 it is judged that any of the parameters has been changed; more specifically, when it is judged that a parameter related to the cross sectional shape $S_{YX}$ has been changed, the processes from S202 are repeatedly executed.

Figure 12:
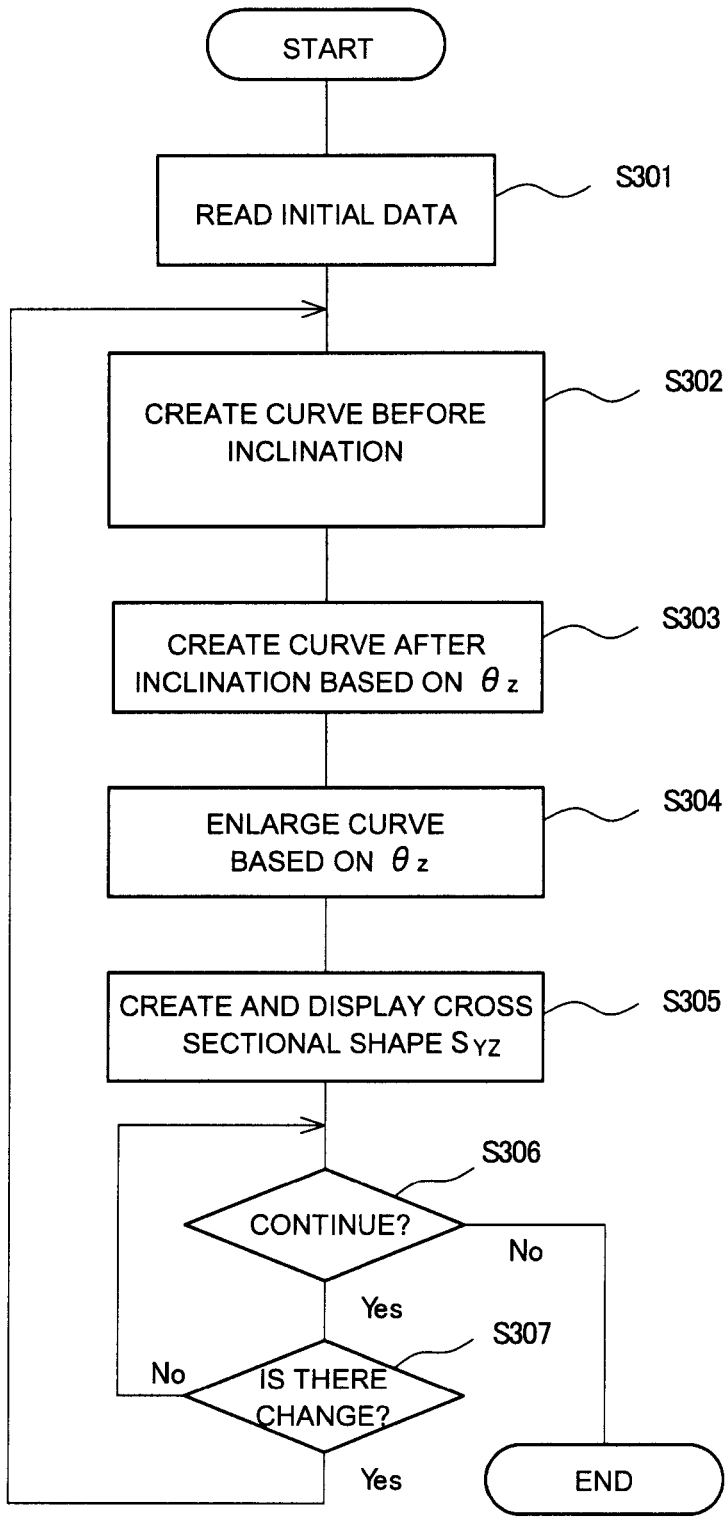
FIG. 12 is a flowchart showing a creation process of the YZ cross sectional shape of the three-dimensional region of interest.

FIG. 12 is a flowchart of the creation process of the cross sectionals shape $S_{YZ}$ shown in (B) in FIG. 10. The content is basically identical to the content of FIG. 11, and, thus, will be briefly described.

In S301, initial data is referred to, and, in S302, a parameter set is referred to and a curve which is not inclined is created based on the parameter set. In S303, an inclination process is executed based on the inclination angle $\theta_Z$ in the Z direction, and an inclined curve is created. In S304, an enlargement percentage is determined based on the inclination angel $\theta_Z$, and a curve after enlargement is created as a result of application of the enlargement process on the inclined curve. In S305, the cross sectional shape $S_{YZ}$ including the enlarged curve is determined and is displayed over the tomographic image. In S306, it is judged whether or not the above-described process is to be continued, and, if the process is to be continued, in S307 it is judged whether or not a value of a parameter which affects the cross sectional shape $S_{YZ}$ has been changed. When it is judged that a parameter has been changed, the processes from S302 are executed repeatedly.

In the above-described embodiment, because the process in the creation of the cross sectional shape is mainly in the two-dimensional space, there can be obtained an advantage that the process can be quickly executed.

(2) Improvement of Image Quality of Three-Dimensional Image (Removal or Reduction of Striped Pattern Noise)

As has already been described, when the rendering start surface (or rendering end surface) is set as a curved surface, a striped pattern (striped pattern noise) which is unnecessary tends to be generated on the three-dimensional image. A method of solving this problem will now be described. The process described below is executed by the volume rendering unit 20 shown in FIG. 1. Conditions necessary for this process are provided from the controller 36.

Figure 13:
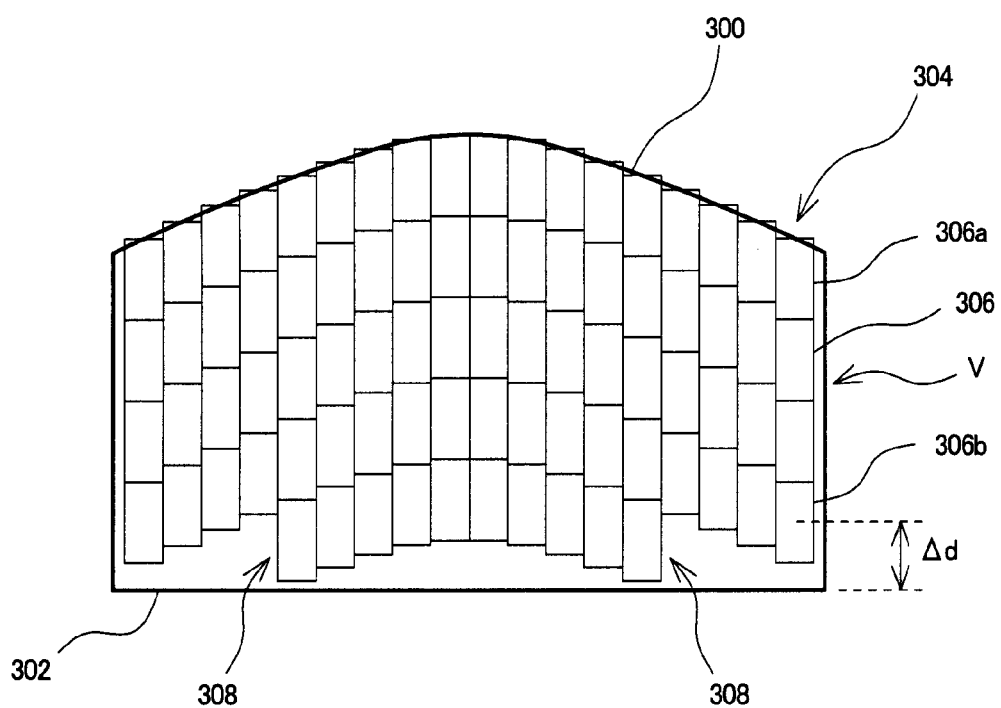
FIG. 13 is a diagram showing a phenomenon where positions of end points become non-uniform among a plurality of rays.

FIG. 13 schematically shows a three-dimensional region of interest V. The three-dimensional region of interest V comprises a clipping plane 300, which is a two-dimensionally curved plane and which forms the rendering start surface in this example configuration. A plurality of rays (calculation paths) 304 are set for the three-dimensional region of interest V. On each ray 304, normally, a plurality of sampling points 306 are defined with a certain pitch. A start point which is the first sampling point is defined by the clipping plane 304 functioning as the rendering start surface. Normally, the start point is defined on the clipping plane 304. In FIG. 13, an individual sampling point is represented as a rectangular box having a predetermined length. In each sampling point, for example, 8 data points existing around the sampling point are referred to, and, with an interpolation calculation based on these data points, data of the sampling point (voxel data) are generated. Next, for each sampling point, for example, the following voxel calculation is executed.

$$C_{OUTi} = (1-\alpha_i) \cdot C_{INi} + \alpha_i \cdot e_i \quad (1)$$

In the above-described equation, $C_{OUTi}$ represents an amount of output light (output brightness value) of an ith voxel and $C_{INi}$ represents an amount of input light (input brightness value) of the ith voxel. $C_{INi}$ is the amount of output light of the (i−1)th voxel, $C_{OUTi-1}$. A parameter $\alpha_i$ represents opacity (degree of unclearness), and $(1-\alpha_i)$ consequently represents clearness. A parameter $e_i$ represents an echo value of the ith voxel (voxel value generated by interpolation calculation). In other words, the calculation of the amount of output light is executed for each voxel (voxel calculation). The voxel calculation is sequentially and repeatedly executed from the start point.

As an ending condition of the voxel calculation, normally two end conditions are determined. A first ending condition is a condition to define that the voxel calculation is to end when the next voxel calculation exceeds an end surface 302. This is a condition for forming an image of only the inside of the three-dimensional region of interest V. The second ending condition is, for example, a condition to define that the voxel calculation is to end when the amount of output light reaches a maximum value.

Figure 14:
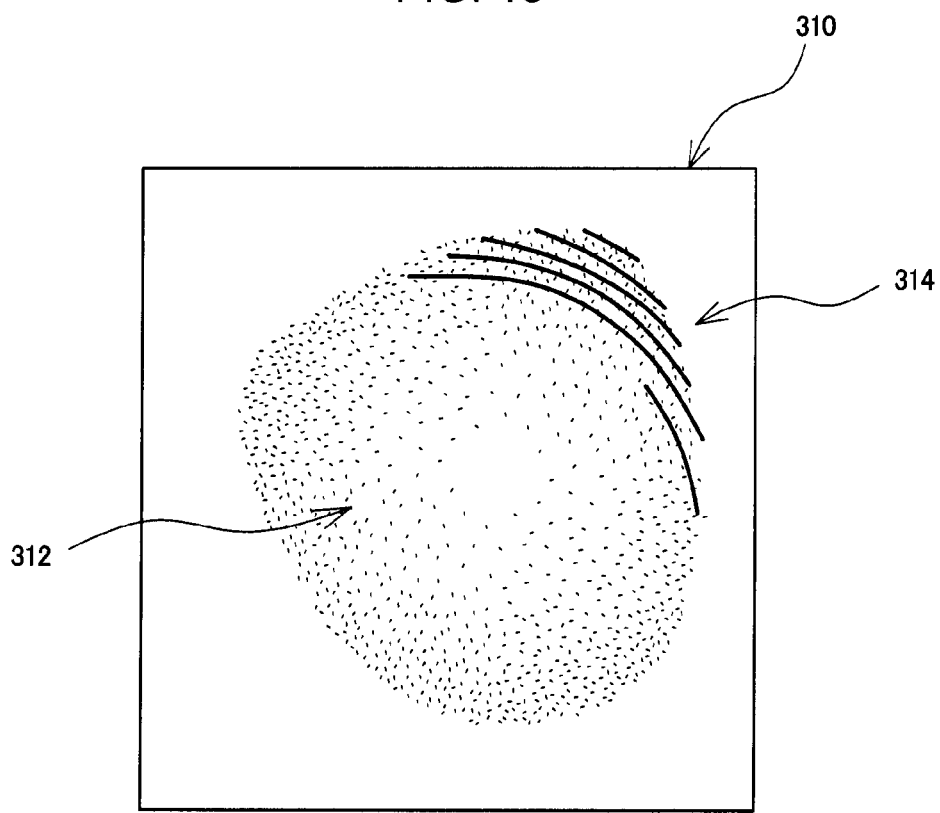
FIG. 14 is a diagram showing a striped pattern formed on a three-dimensional image.

Because the rendering start surface is curved, the sampling positions are not uniform among the plurality of rays. For the same reason, the position of the final voxel (voxel at the time when the ending condition is met) in each ray 304 is also not uniform, and the distance to the rendering end surface 302 would differ for each ray (refer to FIG. 13). When observed in the horizontal direction, a step 308 of number of data points also occurs. Because the distance to the rendering end surface 302 changes in a periodic manner, the periodicity tends to appear in the image. FIG. 14 schematically shows a three-dimensional image. For the reason shown in FIG. 13, an unnecessary striped pattern 314 is caused in addition to the three-dimensional image of the tissue. The striped pattern reflects the form of the curvature of the clipping plane, and a striped pattern of a multiple-ring shape or a striped pattern of multiple parallel lines may be formed. Such a striped pattern is a significant obstruction in observation of the image, and surprises the examinee who does not know the circumstances.

Figure 15:
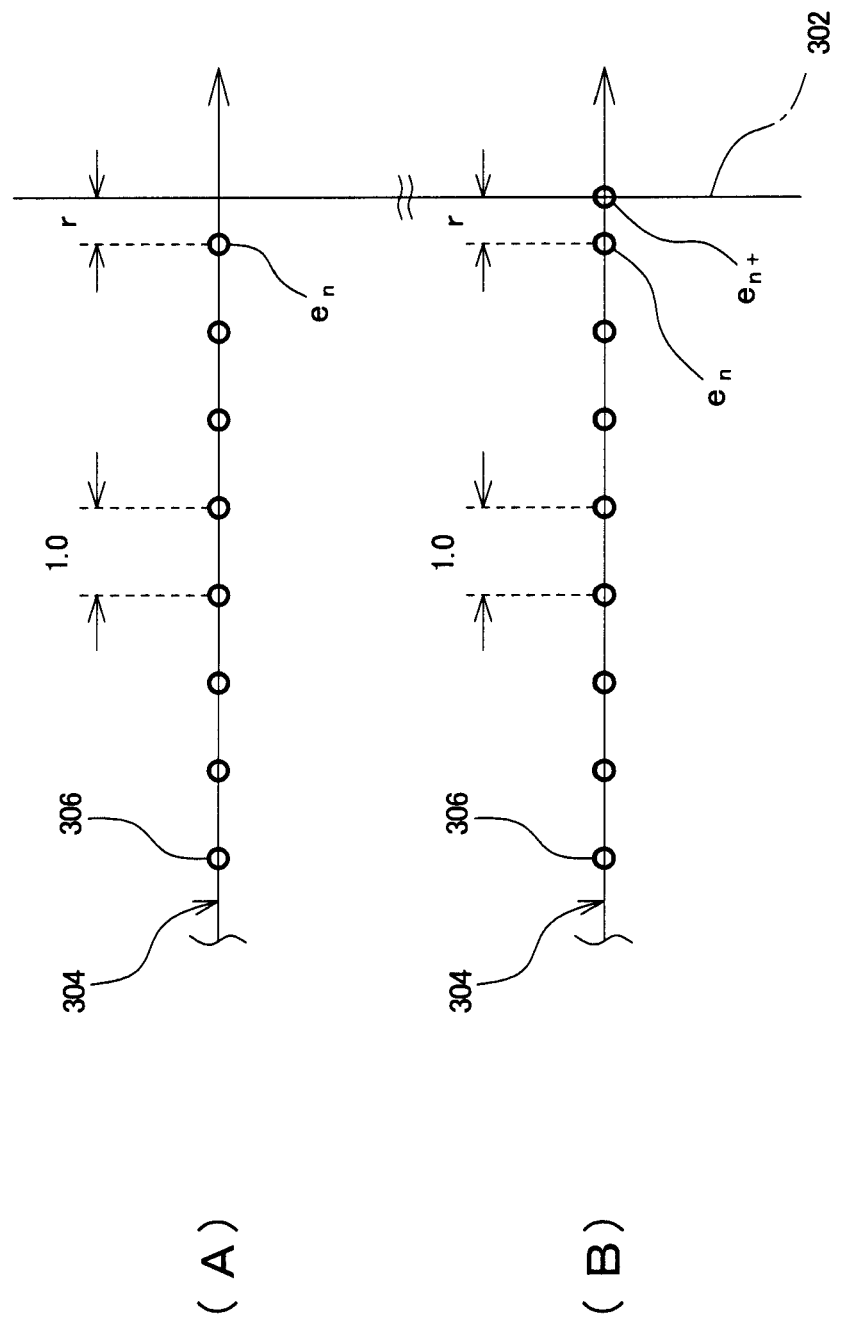
FIG. 15 is a diagram for explaining two methods for inhibiting formation of the striped pattern.

FIG. 15 exemplifies two methods for solving this problem. A method (A) represents a first example method, and a method (B) represents a second example method. In the first example method, a plurality of sampling points (voxels) 306 are defined on the ray 304. The interval between the sampling points is a constant, and is an interval of 1.0 in FIG. 15. Reference numeral 302 represents the end surface. A distance r exists as a gap between the final voxel En and the end surface 302. The distance r has a value of less than 1.0. In the first example method, a calculation represented by the following equation (2); that is, a calculation including weighting, is executed in place of the calculation with the equation (1) as an exceptional process for only the final voxel.

$$C_{OUTn} = (1-\alpha_n) \cdot C_{INn} + \alpha_n \cdot e_n \cdot r \qquad (2)$$

In equation (2), $C_{OUTn}$ represents the amount of output light of the final voxel. In other words, while in the related art, the echo value of the final voxel has been used for the voxel calculation, in the first example method, a weight by the parameter r is applied to the echo value of the final voxel, wherein $0 \leq r < 1.0$. By applying such a weighting process based on the distance r to each ray, it is possible to reduce or resolve the steps in the brightness value which occur in a periodic manner in the direction of alignment of the rays.

Next, a second example method shown by (B) will be described. Whereas the voxel having an echo value $e_n$ is the final voxel in the method of related art, in the second example method, the final voxel is a voxel having the next echo value $e_{n+}$. The final voxel is forcefully set on the end surface 302. For the final voxel, a calculation of equation (3) is executed as an exception in place of the calculation of equation (1).

$$C_{OUTn+} = (1-\alpha_{n+}) \cdot C_{INn+} + \alpha_{n+} \cdot e_{n+} \cdot r \qquad (3)$$

In equation (3), $C_{OUTn+}$ is the amount of output light which is finally output, and is converted to the brightness value. Such a process is applied to each ray. Compared to the first example method, because the pixel value can be determined using the echo values up to the echo value on the end surface 302 in the second example method, an image process faithful to the shape of the three-dimensional region of interest can be realized. In particular, the distance to the final surface does not differ among the rays, and, because the weight based on the distance r from the previous voxel is applied to the echo value which is finally added to each ray, the periodicity of the brightness change in the direction of alignment of the ray can be reduced, and, in particular, occurrence of the step in the brightness value can be sufficiently reduced and resolved. In equations (2) and (3), when the opacity α is determined based on the echo value e, the opacity α is determined for the final voxel based on a result of multiplication of the echo value e and the weight r.

Figure 16:
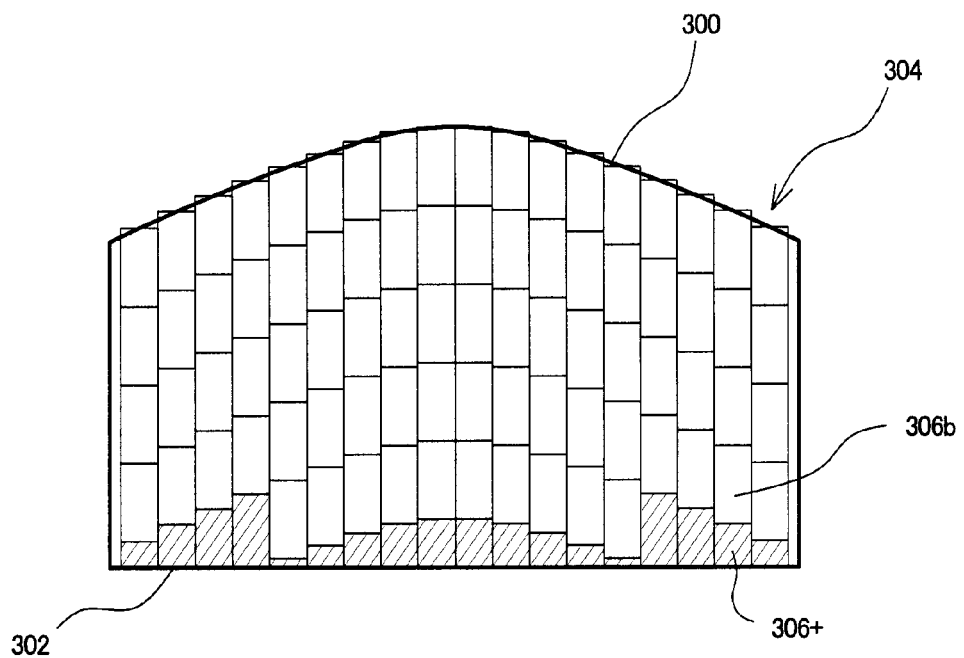
FIG. 16 is a diagram showing a method of matching the plurality of end points for the plurality of rays.
Figure 17:
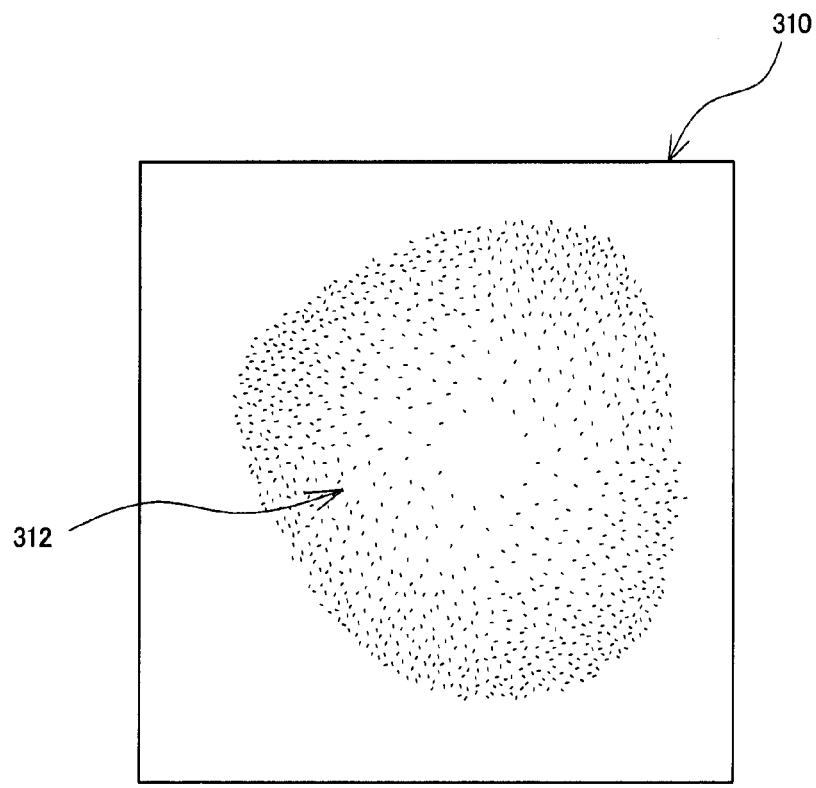
FIG. 17 is a diagram showing elimination of the striped pattern through application of the method of a preferred embodiment of the present invention.

FIG. 16 shows a calculation target range when the second example method is applied. In FIG. 16, reference numeral 306b represents a voxel previous to a final voxel 306+. Because the contribution of the final voxel 306+ among rays depends on the distance r from the previous voxel 306b to the end surface 302, the step can be effectively resolved. FIG. 17 schematically shows results of three-dimensional image process when the first example method and the second example method are applied. The striped pattern 314 shown in FIG. 14 has now disappeared. With such a process, the noise which is obstructive for observation can be reduced, and the image quality can be improved.

In the first and second example methods described above, the distance r acts on the final echo value, but alternatively, the distance r may act directly on the opacity or directly on the brightness value.

In the above-described embodiment, a solution method for a problem caused by periodical change of the distance between the end surface and the final voxel has been described, but the application of the method is not limited to such a configuration, and a method similar to the above-described method may be applied to a case where the positions of the sampling points are matched among rays instead of the start voxel on the ray being matched to the curved start surface. More specifically, in such a case, a fractional distance is caused between the start voxel and the start surface. Therefore, the distance may be recognized as the weight, and the calculation condition may be modified to reflect the distance on the pixel value. Alternatively, a smoothing process along the direction of alignment of the rays, techniques for randomly correcting the brightness value or echo value, etc. may be combined with the above-described method. In any case, it is desirable to suitably correct the rendering condition to reduce the periodicity and minimize degradation of the original image. The necessity or unnecessity of the partial correction may be selected by the user or may be automatically determined based on an image evaluation result.

What is claimed is:

1. An ultrasonic volume data processing device comprising:
   a three-dimensional region-of-interest setting unit which sets a three-dimensional region of interest for a rendering process with respect to ultrasonic volume data obtained from a three-dimensional space in a living body; and
   a three-dimensional ultrasonic image forming unit which executes the rendering process using data in the three-dimensional region of interest, to form a three-dimensional ultrasonic image, wherein
   the three-dimensional region of interest has a clipping plane which spatially separates a target tissue and a non-target tissue, and
   the three-dimensional region-of-interest setting unit comprises:
   a deformation unit which deforms the clipping plane; and
   an inclination unit which causes an entirety of the clipping plane to be inclined with respect to the ultrasonic volume data.

2. The ultrasonic volume data processing device according to claim 1, wherein
   the deformation unit deforms the clipping plane into a convex shape or a concave shape.

3. The ultrasonic volume data processing device according to claim 2, wherein
   the clipping plane has a first horizontal direction, a second horizontal direction, and a vertical direction as three directions of inclination movement, and
   the deformation unit determines a height in the vertical direction for a representative point of the clipping plane according to a parameter h designated by a user.

4. The ultrasonic volume data processing device according to claim 3, wherein shapes on respective sides of the representative point are in a line symmetric relationship in the first horizontal direction, and shapes on respective sides of the representative point are in a line symmetric relationship in the second horizontal direction.

5. The ultrasound volume data processing device according to claim 1, wherein the inclination unit determines a two-dimensional inclination orientation of the clipping plane according to a first inclination angle θ1 and a second inclination angle θ2.

6. The ultrasonic volume data processing device according to claim 1, further comprising:

a size adjustment unit which adjusts a size of the clipping plane according to an inclination angle of the clipping plane.

7. The ultrasonic volume data processing device according to claim 6, wherein the size adjustment unit increases the size of the clipping plane as the inclination angle of the clipping plane is increased.

8. The ultrasonic volume data processing device according to claim 7, wherein in a first step, the deformation unit creates a clipping plane after deformation;

in a second step after the first step, the inclination unit causes the clipping plane after deformation to be inclined, to create a clipping plane after deformation and inclination; and in a third step after the second step, the size adjustment unit adjusts the size of the clipping plane after deformation and inclination, to create a clipping plane after deformation, inclination, and size adjustment.

9. The ultrasonic volume data processing device according to claim 8, wherein the deformation unit creates first three-dimensional shape data as the clipping plane after deformation;

the inclination unit creates second three-dimensional shape data as the clipping plane after deformation and inclination by a rotational conversion of the first three-dimensional shape data;

the size adjustment unit creates third three-dimensional shape data as the clipping plane after deformation, inclination, and size adjustment by an enlargement conversion of the second three-dimensional shape data; and a voxel calculation start point on each ray when the rendering process is executed is defined based on the third three-dimensional shape data.

10. The ultrasonic volume data processing device according to claim 1, further comprising:

a tomographic image forming unit which forms a first tomographic image and a second tomographic image which are orthogonal to each other, based on the ultrasonic volume data;

a graphic image forming unit which forms a first graphic image and a second graphic image representing two cross sections of the three-dimensional region of interest which are orthogonal to each other; and a display unit which displays a first display image in which the first graphic image is combined over the first tomographic image and displays a second graphic image in which the second graphic image is combined over the second tomographic image, wherein when the three-dimensional region of interest is changed, contents of the first graphic image and the second graphic image are changed in connection with the change of the three-dimensional region of interest.

11. The ultrasonic volume data processing device according to claim 1, further comprising:

a storage unit which stores a plurality of initial parameter sets; and a selection unit which selects a particular parameter set from the plurality of initial parameter sets, wherein the three-dimensional region-of-interest setting unit sets an initial three-dimensional region of interest according to the particular parameter set.

12. The ultrasonic volume data processing device according to claim 1, wherein the target tissue is a fetus, and the non-target tissue is a womb or a placenta.

13. The ultrasonic volume data processing device according to claim 1, wherein the three-dimensional ultrasonic image forming unit forms the three-dimensional ultrasonic image by setting a plurality of rays for the three-dimensional region of interest and repeatedly executing a voxel calculation along each ray, and the plurality of voxel calculations for each ray include a special voxel calculation for inhibiting occurrence of a striped pattern caused by at least one of a start surface and an end surface in the three-dimensional region of interest being curved.

14. The ultrasonic volume data processing device according to claim 13, wherein the special voxel calculation is a voxel calculation which uses a fraction of less than a certain sampling interval caused when a plurality of sampling points are set for each ray at the certain sampling interval.

15. A non-transient computer readable medium storing a program having a function to set a three-dimensional region of interest for rendering with respect to ultrasonic volume data obtained from a three-dimensional space in a living body and executed by an ultrasonic volume data processing device, the program comprising:

a clipping plane creating module to create a clipping plane which is a plane included in the three-dimensional region of interest and which spatially separates a target tissue and a non-target tissue, wherein the clipping plane creating module comprises:

a deforming function to deform the clipping plane based on an input of a user, and an inclining module to cause an entirety of the clipping plane to be inclined based on an input of the user.

16. An ultrasonic volume data processing device comprising:

a three-dimensional region-of-interest setting unit which sets a three-dimensional region of interest in which a rendering process is applied, with respect to ultrasonic volume data, the three-dimensional region of interest including a clipping plane which spatially separates a target tissue and a non-target tissue; and a three-dimensional ultrasonic image forming unit which forms a three-dimensional ultrasonic image by setting a plurality of rays for the three-dimensional region of interest and repeatedly executing a voxel calculation along each ray, wherein the plurality of voxel calculations for each ray include a special voxel calculation for inhibiting occurrence of a striped pattern caused by a start surface in the three-dimensional region of interest being curved, the start surface being the clipping plane that is deformed based on input information, and the special voxel calculation is a voxel calculation which uses a fraction of less than a certain sampling interval caused when a plurality of sample points are set for each ray at the certain sampling interval.

17. The ultrasonic volume data processing device according to claim 16, wherein
the fraction corresponds to a distance between a voxel which is one voxel before the end surface and the end surface.

18. The ultrasonic volume data processing device according to claim 17, wherein
the special voxel calculation is a voxel calculation for an end voxel determined based on the end surface and in which the distance acts as a weight value.

19. The ultrasonic volume data processing device according to claim 18, wherein
the end voxel is a voxel determined by the certain sampling interval.

20. The ultrasonic volume data processing device according to claim 19, wherein
the end voxel is a voxel which is additionally set on the end surface and which is not determined by the certain sampling interval.

21. A non-transient computer readable medium storing a program for execution in an ultrasonic volume data processing device which processes ultrasonic volume data, the program comprising:
a module to set a three-dimensional region of interest in which a rendering process is applied, with respect to the ultrasonic volume data, the three-dimensional region of interest including a clipping plane which spatially separates a target tissue and a non-target tissue; and
a module to form a three-dimensional ultrasonic image by setting a plurality of rays for the three-dimensional region of interest and repeatedly executing a voxel calculation along each ray, wherein the plurality of the voxel calculations for each ray include a special voxel calculation for inhibiting occurrence of a striped pattern caused by a start surface in the three-dimensional region of interest being curved, the start surface being the clipping plane that is deformed based on input information, and
the special voxel calculation is a voxel calculation which uses a fraction of less than a certain sampling interval caused when a plurality of sample points are set for each ray at the certain sampling interval.

22. A method for ultrasonic volume data processing comprising:
setting a three-dimensional region of interest for a rendering process with respect to ultrasonic volume data obtained from a three-dimensional space in a living body, the three-dimensional region of interest including a clipping plane which spatially separates a target tissue and a non-target tissue;
deforming the clipping plane;
causing an entirety of the clipping plane to be inclined with respect to the ultrasonic volume data; and
executing the rendering process using data in the three-dimensional region of interest, to form a three-dimensional ultrasonic image.

23. A method for ultrasonic volume data processing comprising:
setting a three-dimensional region of interest in which a rendering process is applied, with respect to ultrasonic volume data, the three-dimensional region of interest including a clipping plane which spatially separates a target tissue and a non-target tissue; and
forming a three-dimensional ultrasonic image by setting a plurality of rays for the three-dimensional region of interest and repeatedly executing a voxel calculation along each ray, wherein
the plurality of voxel calculations for each ray include a special voxel calculation for inhibiting occurrence of a striped pattern caused by a start surface in the three-dimensional region of interest being curved, the start surface being the clipping plane that is deformed based on input information, and
the special voxel calculation is a voxel calculation which uses a fraction of less than a certain sampling interval caused when a plurality of sample points are set for each ray at the certain sampling interval.

* * * * *